(12) United States Patent
Sayeram et al.

(10) Patent No.: US 8,721,080 B2
(45) Date of Patent: May 13, 2014

(54) SYSTEMS FOR IMAGING STRUCTURES OF A SUBJECT AND RELATED METHODS

(71) Applicant: Bioptigen, Inc., Morrisville, NC (US)

(72) Inventors: Sunita Sayeram, Durham, NC (US); Joseph Elliott Vance, Durham, NC (US); Pete Huening, Clayton, NC (US); Eric L. Buckland, Hickory, NC (US); Joseph A. Izatt, Raleigh, NC (US); Glenn A. Myers

(73) Assignee: Biopgtigen, Inc., Morrisville, NC (US)

( * ) Notice: Subject to any disclaimer, the term of this patent is extended or adjusted under 35 U.S.C. 154(b) by 0 days.

(21) Appl. No.: 14/020,945

(22) Filed: Sep. 9, 2013

(65) Prior Publication Data

US 2014/0020683 A1 Jan. 23, 2014

Related U.S. Application Data

(63) Continuation of application No. 13/545,239, filed on Jul. 10, 2012, now Pat. No. 8,534,837, which is a continuation of application No. 12/771,032, filed on Apr. 30, 2010, now Pat. No. 8,240,853.

(60) Provisional application No. 61/174,589, filed on May 1, 2009.

(51) Int. Cl.
*A61B 3/14* (2006.01)
*A61B 3/00* (2006.01)

(52) U.S. Cl.
USPC .......................................... 351/208; 351/246

(58) Field of Classification Search
USPC ................................................. 351/200–246
See application file for complete search history.

(56) References Cited

U.S. PATENT DOCUMENTS

| | | | |
|---|---|---|---|
| 4,059,348 A | 11/1977 | Jernigan | 351/224 |
| 5,320,069 A | 6/1994 | Anderson, Jr. et al. | |
| 7,133,713 B2 | 11/2006 | Zan | |
| 7,426,904 B2 * | 9/2008 | Zan et al. | 119/756 |
| 8,240,853 B2 | 8/2012 | Sayeram et al. | 351/208 |
| 2009/0268161 A1 * | 10/2009 | Hart et al. | 351/208 |
| 2012/0327368 A1 * | 12/2012 | Williams et al. | 351/221 |

OTHER PUBLICATIONS de la Cera et al. "Optical Aberrations in the Mouse Eye" *Vision Research* 46:2546-2553 (Mar. 2006).
Hossein-Javaheri et al. "Imaging Retinal Degeneration in Mice by Combining Fourier Domain Optical Coherence Tomography and Fluorescent Scanning Laser Ophthalmoscopy" *Proc of SPIE* 7171 71710Z-1-8 (Feb. 20, 2009).
Hughes. "A Schematic Eye for the Rat" *Vision Research* 19:569-588 (Mar. 19, 1979).

(Continued)

*Primary Examiner* — Mohammed Hasan
(74) *Attorney, Agent, or Firm* — Myers Bigel Sibley & Sajovec

(57) ABSTRACT

Systems for imaging structures of a subject are provided. The subject has an optical axis, a pupil, and a nodal point. The system includes an image capture device; a first structure including a mount for the subject to be imaged by the image capture device, the first structure providing at least two rotational degrees of freedom; a second structure including a mount for the image capture device, the second structure providing at least two translational degrees of freedom; and a means for aligning the image capture device in relation to the optical axis, the pupil, and the nodal point of the subject.

20 Claims, 19 Drawing Sheets

(56) References Cited

OTHER PUBLICATIONS

*Jeon et al. "Mouse Schematic Eye" *The Journal of Neuroscience* 18(21):8936-8946 (Jan. 1998).

Jeon et al. "The Major Cell Populations of the Mouse Retina" *The Journal of Neuroscience* 18(21):8936-8946 (Nov. 1, 1998).

Kim et al. "Monitoring Mouse Retinal Degeneration with High-Resolution Spectral-Domain Optical Coherency Tomography" *Journal of Vision* 8(1):17, 1-11 (Jan. 24, 2008).

Kocaoglu et al. "Simultaneous Fundus Imaging and Optical Coherence Tomography of the Mouse Retina" *Investigative Ophthalmology & Visual Science* 48(3):1283-1289 (Mar. 2007).

Li et al. "Noninvasive Imaging by Optical Coherence Tomography to Monitor Retinal Degeneration in the Mouse" *Investigative Ophthalmology & Visual Science* 42(12):2981-2989 (Nov. 2001).

Panda-Jonas, MD et al. "Retinal photoreceptor count, retinal surface area, and optic disc size in normal human eyes," Ophthalmology, 101(3):519-523 (Mar. 1994).

Remtulla et al. "A Schematic Eye for the Mouse, and Comparisons with the Rat" *Vision Research* 25(1):21-31 (Mar. 1985).

Ruggeri et al. "In Vivo Three-Dimensional High-Resolution Imaging of Rodent Retina with Spectral-Domain Optical Coherence Tomography" *Investigative Ophthalmology & Visual Science* 48(4):1808-1814 (Mar. 2007).

Ruggeri et al. "Retinal Tumor Imaging and Volume Quantification in the Mouse Model Using Spectral-Domain Optical Coherence Tomography" *Optics Express* 17(5):4074-4083 (Feb. 2009).

Srinivasan et al. "Noninvasive Volumetric Imaging and Morphometry of the Rodent Retina with High-Speed, Ultrahigh-Resolution Optical Coherence Tomography" *Investigative Ophthalmology & Visual Science* 47(12):5522-5528 (2006).

Van Eeden et al. "Early Vascular and Neuronal Changes in a VEGF Transgenic Mouse Model of Retinal Neovascularization" *Investigative Ophthalmology & Visual Science* 47(10):4638-4645 (Jun. 2006).

Williams. "Rabbit and Rodent Ophthalmology" *EJCAP* 17(3):242-252 (May 2007).

Yuen. "Feature-Based Classification of Mouse Eye Images" Undergraduate thesis paper, University of Washington, Seattle, WA (31 pages) (Dec. 2006).

Oyster, Clyde W. , "The Human Eye," Sinauer Associates, Inc., Sunderland, Massachusetts, 1999, pp. 753-766, March.

* cited by examiner

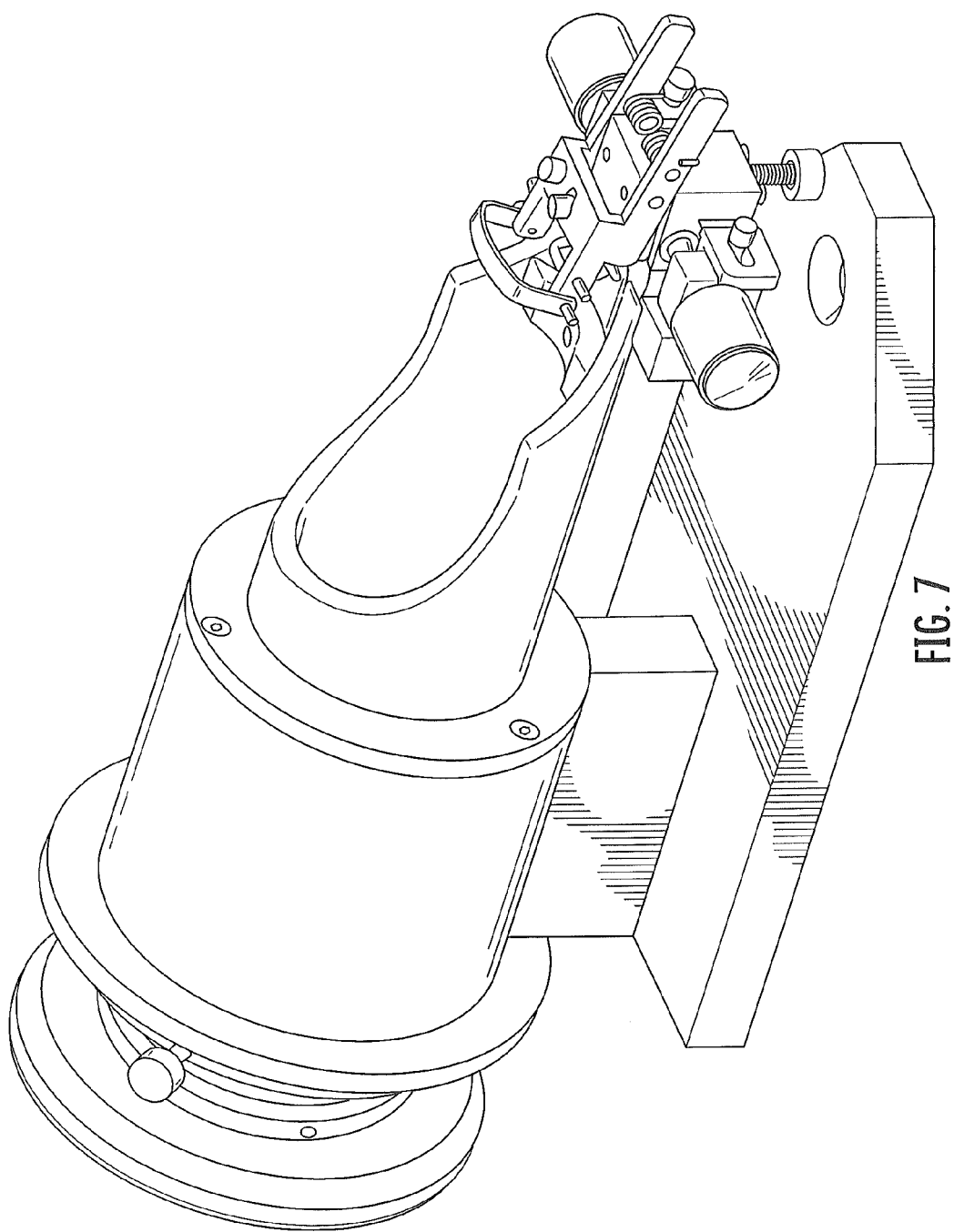

SYSTEMS FOR IMAGING STRUCTURES OF A SUBJECT AND RELATED METHODS

CLAIM OF PRIORITY

The present application is a continuation of U.S. application Ser. No. 13/545,239, filed Jul. 10, 2012, now U.S. Pat. No. 8,534,837, which is a continuation of U.S. application Ser. No. 12/771,032, filed Apr. 30, 2010, now U.S. Pat. No. 8,240,853, which claims priority to U.S. Provisional Application No. 61/174,589, filed May 1, 2009, the disclosures of which are hereby incorporated herein by reference as if set forth in their entirety.

FIELD

The present invention relates generally to imaging systems and, more particularly, to high-throughput imaging systems for fine alignment of an eye of a subject for ophthalmic imaging applications.

BACKGROUND

Preclinical imaging of small animals, for example, rodents, is important in drug development and research exploring genetics and the early diagnosis of diseases. Several neurological conditions have a manifestation in retinal tissue, and can present as lesions in the retinal layers at very early disease stages. Thus, there is much utility in the ability to diagnose disease by identifying structural changes in the retinal layers, starting with piscine (fish) and murine (rodent) models.

Precise alignment of the rodent eye to an optical system, for example, optical coherence tomography (OCT) imaging systems has been a challenge for researchers. Rodents have been historically hard to image because of, for example, the small eye size, poor imaging properties of the eye, and lack of stage that enables the precise alignment of a rodent eye to the optical beam of a fundus camera or clinical OCT scanner. The development of a hand-held OCT probe, while enabling breakthroughs not previously possible, has not made the task much easier by itself, due to the lack of fine control over the angles between the optical axis of the OCT probe and the axis of the rodent eye. The mouse eye has an approximate diameter of 3.3 mm, while the rat eye diameter is around 6.4 mm, and thus, manipulations on a micro level are typically necessary to enable the acquisition of good quality images of the rodent retina. The ball lens phenotype of the rodent eye compared to the human eye typically requires very different optics to capture images of the layers in as fine detail. The design of the specific optics is discussed in commonly assigned United States Patent Publication No. 2009/0268161, published on Oct. 29, 2009, entitled OPTICAL COHERENCE TOMOGRAPHY (OCT) IMAGING SYSTEMS HAVING ADAPTABLE LENS SYSTEMS AND RELATED METHODS AND COMPUTER PROGRAM PRODUCTS.

SUMMARY

Some embodiments discussed herein provide systems for imaging structures of a subject. The subject has an optical axis, a pupil, and a nodal point. The system includes an image capture device; a first structure including a mount for the subject to be imaged by the image capture device, the first structure providing at least two rotational degrees of freedom; a second structure including a mount for the image capture device, the second structure providing at least two translational degrees of freedom; and a means for aligning the image capture device in relation to the optical axis, the pupil, and the nodal point of the subject.

In further embodiments, axes of the at least two rotational degrees of freedom of the first structure may intersect. An optical axis of the image capture device mounted on the second structure may be aligned to intersect the intersecting axes of the at least two rotational degrees of freedom of first structure. The mount for the subject in the first structure may be configured such that the optical axis of the subject is aligned to within about 5.0 degrees of the optical axis of the image capture device mounted to the second structure when the subject is positioned in the mount of the first structure. The subject may be aligned to within from about 0.0 degrees to about and 45.0 degrees.

In still further embodiments, the mount of the first structure may be configured such that the axes of the two rotational degrees of freedom intersect at the nodal point of the subject when the subject is positioned in the mount of the first structure. The nodal point of the subject may be approximated by a pupil of the subject.

In some embodiments, an optical axis of the image capture device of the second structure may be rotated about the nodal point of the subject of the first structure such that an angle between the optical axis of the image capture device and the optical axis of the subject sweeps through a cone of at least about 15.0 degrees in at least two non-co-planar directions.

In further embodiments, an optical axis of the image capture device of the second structure may be rotated about the nodal point of the subject of the first structure such that an angle between the optical axis of the image capture device and the optical axis of the subject sweeps through a cone of at least about 30.0 degrees in at least two non-co-planar directions.

In still further embodiments, the at least two rotational degrees of freedom of the first structure may include a rotation about a first axis substantially parallel to a first axis of symmetry of the subject and a rotation about an orthogonal second axis substantially parallel to a second axis of symmetry of the subject.

In some embodiments, the subject may be a small animal; and the first axis of symmetry of the small animal may be an axis of the body that separates a right side of the small animal from a left side of the small animal and a right eye of the small animal from a left eye of the small animal. The second axis of symmetry of the small animal may be an axis orthogonal to the axis of the body located such that the pupil of at least one eye of the small animal lies in the plane. The small animal may be one of a rodent, a rabbit, a monkey, a dog, a sheep, a cow, a fish, a spider, a turtle, a snake, a frog, an octopus, a chicken, or a bird of prey.

In further embodiments, the small animal may be one of a mammal, a fish, a bird, a reptile, an amphibian, an insect, or a mollusk. In certain embodiments, the subject may be an animal, for example, a vertebrate or an invertebrate animal.

In still further embodiments, the means for aligning may be identifying an intersection of two axes of rotation of the subject mount; aligning the image capture device such that an optical axis of the image capture device intersects the axes of rotation of the subject mount; positioning the subject such that the nodal point of the subject eye is located at the intersection of these two axes of rotation and an imaging axis of the image capture device; and using the at least two rotational degrees of freedom on the subject mount to a desired region of interest of the subject.

In some embodiments, the image capture device may include one of an ultrasound system, an OCT system, a scanning laser ophthalmoscope system, a digital photography system, a film or video camera, and an observation port.

In further embodiments, the system may further include a bite bar associated with the first structure. The bite bar may be configured to aid positioning the subject in the mount of the first structure. The bite bar may have a translational axis and an elevation axis.

In still further embodiments, the system may further include an alignment aid positioned at the intersection of the axes of the at least two rotational degrees of freedom, the alignment aid including a fiducial and being configured to guide placement of the subject in the mount of the first structure. The fiducial may be an imaging phantom. The imaging phantom may be a ball lens with a front surface and a back surface. The ball lens may include a layered structure on the back surface, the layered structure including features substantially thinner than the imaging depth of field of the image capture device and equal to or greater than an axial resolution of the image capture device.

In some embodiments, the ball lens may include a patterned structure on the back surface, the patterned structure including features substantially smaller than the imaging field of view of the image capture device and equal to or greater than a lateral resolution of the image capture device.

In further embodiments, the first structure may include an attachment structure configured to be used for mounting at least one of a bite bar and an alignment fiducial. The attachment structure may include at least one of a pair of alignment pins and a magnet. The mount for the subject of the first structure may further include an integrated heater for warming the subject. The integrated heater may include flow tubes embedded in the mount configured to hold or flow a warm liquid and/or gas.

In still further embodiments, the integrated heater may include electrically insulated electrical resistance heaters embedded in the mount.

In some embodiments, the image capture device may include an alignment fixture that is configured to physically indicate a proper position of a subject to be imaged with respect to the image capture device. In certain embodiments, the alignment fixture may be removable.

In further embodiments, the alignment fixture of the image capture device and a fiducial of the mount of the first structure may intersect at the proper position for placement of the nodal point of the subject to be imaged.

In still further embodiments, the image capture device and the subject are configured to be rotated and/or translated with respect to one another to support imaging of structures not along the optical axis of the subject or near the nodal point of the subject.

In some embodiments, the mount of the first structure may be configured to rotate the subject from a position aligned to image one eye to a position aligned to image a second eye rapidly without removing the subject from the mount.

Further embodiments provide methods for imaging an eye of an animal subject, the method comprising adjusting a position of a nodal point of an eye of the animal subject such that two orthogonal rotational axes intersect substantially at the nodal point of the eye of the animal subject; and adjusting an optical axis of an observation device to substantially intersect the intersection of the two rotational axis substantially at the nodal point of the subject.

In still further embodiments, the method may further include positioning the animal subject in a mount of a first structure; and positioning an observation device in a mount in a second structure. Positioning the animal subject may include positioning the animal subject in the mount of the first structure using a bite bar. The bite bar may have a translational axis and an elevation axis.

In some embodiments, the observation device may include an image capture device or an object configured to be peered through.

In further embodiments, the nodal point of the eye of the animal subject may be approximated by the approximate center of a pupil of the animal subject.

Still further embodiments provide methods for imaging the retina of a small animal subject, the method including positioning the small animal subject in a mount with at least two degrees of motional freedom; mounting an image capture device on a mount with at least two additional degrees of freedom, the at least two additional degrees of freedom not being coupled to the degrees of freedom of the subject; applying a combination of rotation and translation to position a nodal point of an eye of the small animal subject at an intersection of two orthogonal degrees of motional freedom; and aligning the image capture device such that an optical axis of the image capture device is substantially parallel to an optical axis of the subject and substantially intersects the intersection of the two orthogonal degrees of motional freedom of the subject, substantially at the nodal point of the eye of the small animal subject.

In some embodiments the nodal point of the eye of the small animal subject may be approximated by the approximate center of a pupil of the small animal subject.

In further embodiments, the method may further include adjusting relative positions of the small animal subject and the image capture device along the rotational and translational degrees of freedom to improve the intersection of the rotational and translational axes to optimize brightness of a retinal image.

In still further embodiments, the method may further include imaging off-axis retinal structures by rotating the small animal subject about the nodal point of the eye of the subject.

Some embodiments provide methods for imaging an eye of an animal subject, the method including positioning the animal subject in a mount of a first structure using a bite bar; positioning an observation device in a mount in a second structure; adjusting a position of a nodal point of an eye of the animal subject such that two orthogonal rotational axes intersect substantially at the nodal point of the eye of the animal subject; and adjusting an optical axis of an observation device to substantially intersect the intersection of the two rotational axes substantially at the nodal point of the subject.

BRIEF DESCRIPTION OF THE DRAWINGS

FIG. 7 is a diagram illustrating a mouse cassette with bite bar in accordance with some embodiments.

DETAILED DESCRIPTION

Figure 1:
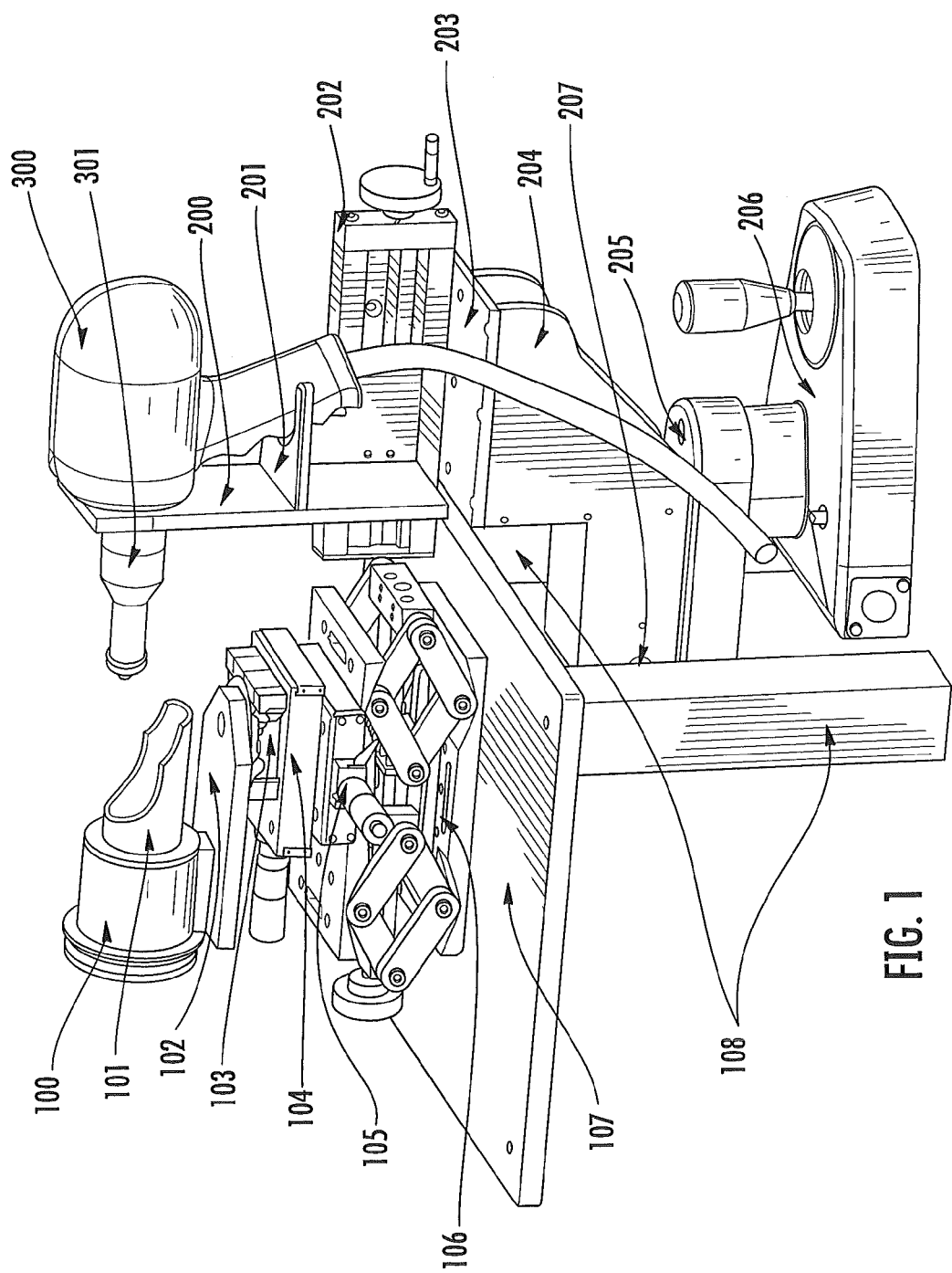
FIG. 1 is a diagram illustrating an Animal Imaging Mount (AIM)-Rodent Alignment Stage (RAS) system in accordance with some embodiments.

Specific exemplary embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the particular exemplary embodiments illustrated in the accompanying drawings is not intended to be limiting of the invention. In the drawings, like numbers refer to like elements.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

As discussed above, preclinical imaging of small animals, for example, rodents, is important in drug development and research exploring genetics and the early diagnosis of diseases. There is a need for an animal mount that enables the handling of rodents, that allows an operator to make fine adjustments to the axes of the animal eye, which can be thought of in terms of a coordinate system in x, y, and z, with two angular adjustments for the azimuthal and elevation angles. To image properly, the optical imaging system has to be aligned to the optical axis and depth of the subject eye using five degrees of freedom—two lateral orthogonal to the optical axis, one parallel to the optical axis, and two rotational degrees about the optical axis, for example, pitch and yaw. Cylindrical symmetry of the eye generally makes roll unnecessary to control. Furthermore, there is the additional need to have a means of monitoring and controlling the animal's core temperature and physiological condition. As the choice of anesthesia may compromise the health of the animal, or at the very least result in motion that may lead to artifacts in the acquired image, the animal stage needs to be adaptable to include an optional bite bar (to reduce head motion) and a nose cone for administering gaseous anesthesia if desired.

U.S. Pat. No. 7,426,904 to Zan et al., U.S. Pat. No. 7,133,713 to Zan and U.S. Pat. No. 5,320,069 to Anderson et al. discuss a need for a small animal holder. Furthermore, *Simultaneous fundus imaging and optical coherence tomography of the mouse retina* (*Invest Ophthalmol. Vis Sci.* 2007; 48(3): 1283-1289) to Koçaoglu et al. discusses an animal stage design specifically for coupling with an OCT system, but none of these approaches addresses the need to be able to identify, control, and rotate about the optical axis of the rodent eye in a systematic, deterministic manner. Aligning to the nodal point of the subject eye is important because it makes for rapid optimization of image quality and enables easy deterministic exploration of the subject eye with simple, small systematic adjustments. Without aligning to the nodal point, imaging of posterior structures of the subject eye may be very difficult. In particular, even slight misalignments may cause serious degradations in image quality, particularly in imaging using OCT.

It is important to design a system that incorporates all of the elements for precision imaging of the ocular system of these animal models. These requirements include, for example, a) optics suitable for the specific animal model as discussed in United States Patent Publication No. 2009/0268161 discussed above; b) an alignment stage with an appropriate management of the degrees of freedom required to aim and focus on the ocular structure; c) a bite bar for positioning and restraining the subject; and d) a methodology for rapid positioning of the subject and aligning of the optics. Additional accessories may facilitate the imaging process. A bite bar designed for the subject and the alignment system facilitates accurate rapid positioning of the eye. An ocular phantom is an additional need that may be useful in mimicking the subject for practice, system validation, and calibration of the system. A system for heating, anesthetizing, and delivering therapies to the subject without adversely impacting imaging is desirable to complete the management process.

Accordingly, as will be discussed further below with respect to FIGS. 1 through 19, embodiments of the present invention provide systems and methods for imaging structures that address each of the needs discussed above.

Some embodiments discuss image capture devices. As used herein, an "image capture device" can be any device capable of viewing or capturing an image using embodiments discussed herein. For example, an image capture device may include an ultrasound system, an optical coherence tomography (OCT) system, a scanning laser ophthalmoscope, a digital photography system, or film or video camera and the like without departing from the scope of embodiments discussed herein. As used herein, an "image capture device" may be an observation port for a human observer, and may or may not include any storage, temporary or permanent of the observed or captured image. As used herein, "image capture device", "image observation device" and "observation device" are interchangeable.

Although embodiments discussed herein refer to image capture devices, embodiments are not limited to this configuration. For example, embodiments discussed herein may be used with any observation device. As used herein, an "observation device" refers to an image capture device or less particularly a device that a user may peer through. Thus, as used herein an observation device is not limited to any particular image capture device, such as OCT or ultrasound. Although ultrasound is not an optical system, and not subject to optical constraints, it is frequently important to correlate optical images to ultrasound images. Therefore, it remains useful to consider aligning an ultrasound system to the subject eye as if it were optical.

Some embodiments of the present invention provide, high-throughput rodent ophthalmic imaging systems including a set of optics matched to the ocular structure of rodents; a path length management system to match the focus to the interferometric condition for OCT imaging of subject eyes with varying focal conditions and optical path lengths; fiducial markers for guiding optimal positioning of the nodal point of a subject eye; capability to switch alignment from one eye to another eye with a simple rotation; and/or accessories for fine-tuning position of animal nodal point; and/or positional recordings to guide the rapid and accurate placement of animals.

As used herein, a "small animal" refers to an animal weighing generally less than about 5 pounds that may be readily placed in a mount or cassette with motional degrees of freedom for adjusting the position and orientation of a nodal point of the animal eye to the optical axis of an image capture device or observation device. A small animal may be murine (rodent) or piscine (fish), but may more generally be of a class of vertebrate or invertebrate models, or stated alternatively may be of a class of mammals, fish, insects, reptiles, amphibians, mollusks, or birds without loss of generality. Although embodiments of the present invention are discussed herein with respect to small animals and, in particular, rodents, as the subjects, embodiments discussed herein are not limited to small animals. The subject could be any subject capable of being imaged using systems and methods discussed herein. For example, the subject may be a rodent, a rabbit, a monkey, a dog, a sheep, a cow, a fish, a spider, a turtle, a snake, a frog, an octopus, a chicken, or a bird of prey or the like without departing from the scope of the present application. Animals larger than about 5 pounds could readily be mounted in structures appropriately sized.

Some embodiments discussed herein provide a mechanism for optimally aligned high-quality images of an eye of a subject, for example, a rodent eye, and increased field-of-view imaging through rotations around the nodal point of the subject eye. As used herein, a "nodal point" of a thin optical system refers to an abstract point in the optical system where a light ray entering the nodal point appears to exit the nodal point in the same direction. A nodal point is an abstract or mathematical concept. Thus, in some embodiments discussed herein, the nodal point of the subject may be approximated by the approximate center of the pupil of the subject eye.

Systems in accordance with some embodiments have the appropriate degrees of freedom to identify, align and steer around the nodal point, making for high-throughput imaging. As will be discussed further below with respect to FIGS. 1 through 19, systems in accordance with some embodiments of the present invention include a mount for an imaging probe, which can be steered toward a rotary small animal stage. The small animal stage may include a cassette sized to hold the small animal subject, and may offer fine translation along the x, y, z axes on a micro scale, and adjustment of azimuthal and elevation angles of the cassette, and may include a bite bar with additional degrees of freedom to precisely tune the position of the nodal point of the eye to the center of rotation of the rotary stage. In some embodiments, the system can be modified to include a heated mount or cassette for temperature control, a nose cone for the administration of gas anesthetics, and/or an injection guide assembly which may also be used for the administration of eye drops. Specially designed optics and reference position may be modified to enable the OCT imaging of either or both of posterior segments (e.g. retina) and anterior segment (e.g. cornea) of the subject eye as will be discussed further herein.

Figure 15:
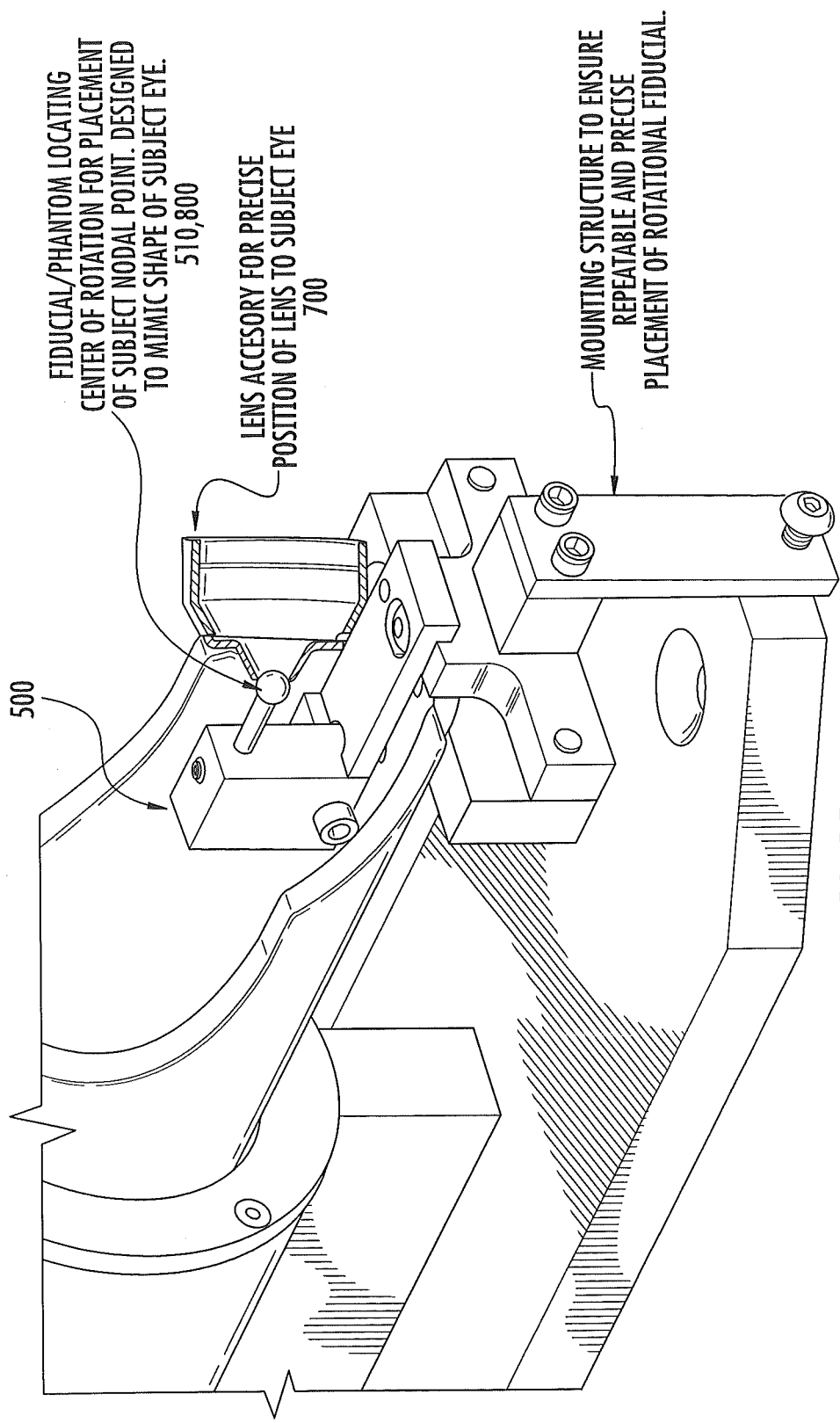
FIG. 15 is a diagram illustrating a centration fiducial, lens adapter, and phantom in accordance with some embodiments.
Figure 16A:
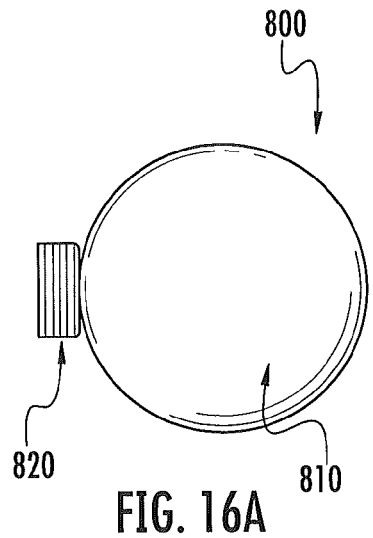
FIGS. 16A through 16C are diagrams illustrating optical phantoms in accordance with some embodiments.
Figure 16B:
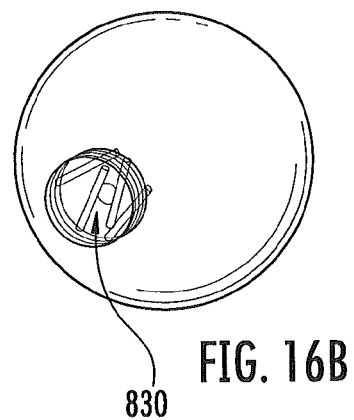
Figure 16C:
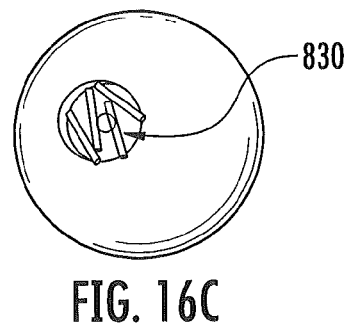

Some embodiments discussed herein provide means for aligning the image capture device in relation to the optical axis, the pupil, and the nodal point of the subject. As shown in FIG. 15, this means may be provided by, for example, calibrating the position of an aiming fiducial 510 such that the fiducial 510 is placed at the intersection of two axes of rotation of the subject mount; aligning the image capture device such that the optical axis of the image capture device intersects the axes of rotation of the subject mount, and that this intersection coincides with the position of the fiducial; applying the aiming tip 700 to the subject-appropriate lens on the image capture device and using the z-axis control of screw-drive 202 (FIG. 1) of the aiming mount, bringing the aiming tip to the fiducial 510, locking the aiming mount such that all degrees of freedom except for the screw-drive are fixed, and marking the position of the screw drive; retracting the position of the image capture device using the screw drive, allowing space for placement of the subject; removing the aiming fiducial and attaching the bite bar; positioning the subject into the appropriate cassette mounted on the rotation structure, and securing the subject to the bite bar; bringing the lens of the image capture device with aiming tip back in place to the nodal position using the screw-drive 202, referring to position marked when aligning to the fiducial; using the motional adjustments on the bite bar and the subject cassette, bringing the subject eye into position at the aiming tip; removing the aiming tip; initiating image capture, such as OCT scanning; adjusting the OCT reference arm such that the target structure is in view; fine tuning the vertical and lateral position of the subject eye using adjustments on the bite bar to optimize image quality; using the rotational degrees of freedom on the subject mount to centrate the image, making final adjustments using micro-adjustments on the Cartesian (x,y) controls of the animal mount; steering with the rotational degrees of freedom of the animal mount to re-center the image to off-axis regions of interest In some embodiments, axes of the at least two rotational degrees of freedom intersect. It will be understood that the axes do not necessarily intersect at a specific angle as the angle changes during rotation.

As will be discussed further herein, in some embodiments of the present invention, the system can be modified to include accessories for intervention while imaging that can be used without moving the nodal point of the animal, to provide a high-throughput rodent imaging stage coupled to a spectral domain OCT system.

In some embodiments of the present invention, high-throughput rodent imaging systems may be coupled with a fundus camera. The system may further include a facility for mounting of an imaging probe, a facility for swapping optics (from specialized mouse optics to rat optics) and/or a capability to do anterior segment imaging (cornea).

In some embodiments of the present invention, high-throughput rodent imaging systems may be coupled with a fundus camera. The system may further include a facility for mounting of an imaging probe and a facility for interchanging imaging optics, for example, from specialized mouse optics to rat optics or from posterior imaging optics to anterior imaging optics.

In some embodiments of the present invention, the small animal imaging system may include a model eye phantom for mimicking the subject that is useful for system alignment, calibration and maintenance. The model eye phantom may include optical characteristics functionally similar to the subject eye, or may be non-optical to be used as a physical placement guide.

Figure 2:
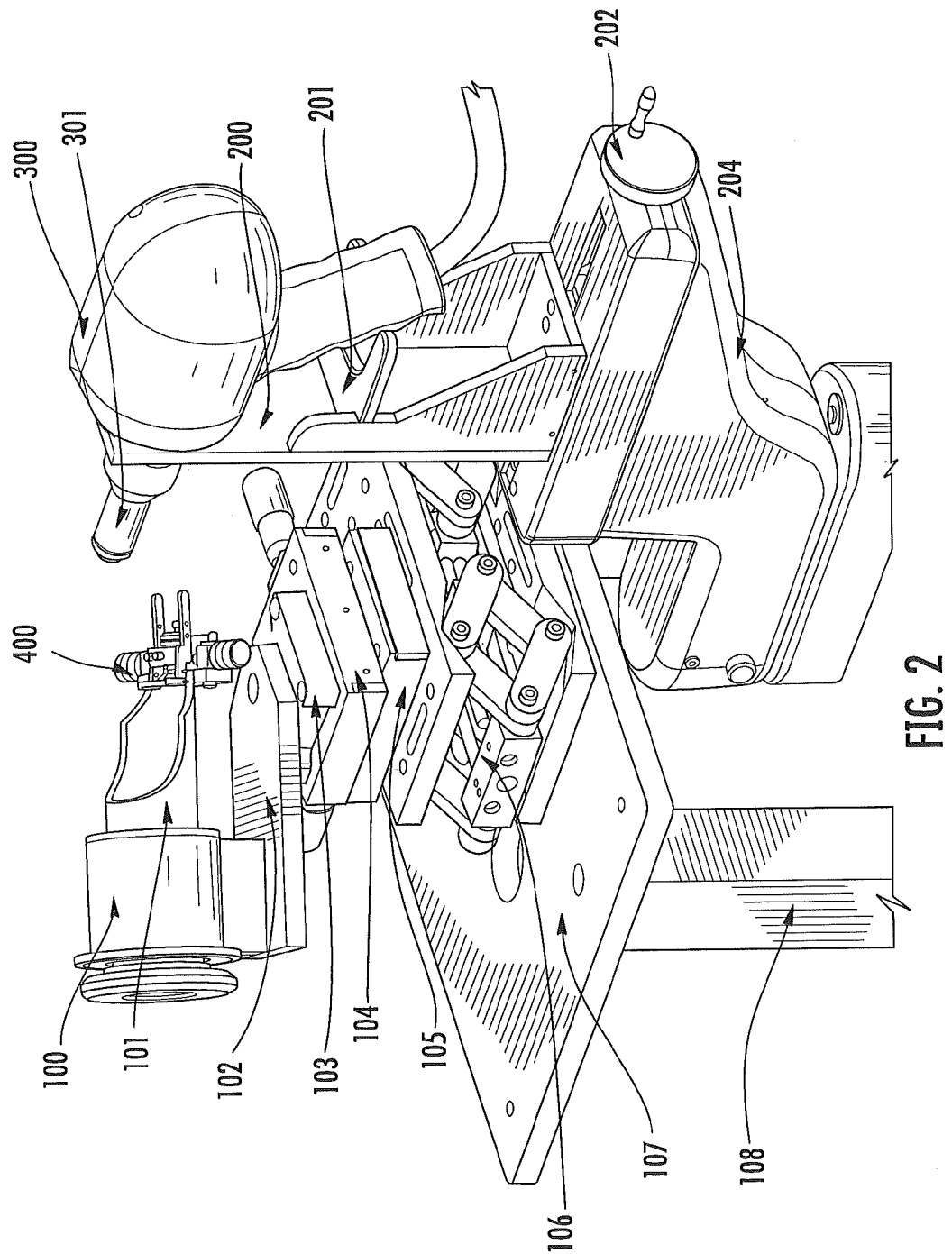
FIG. 2 is a diagram illustrating an AIM-RAS system modified to include a bite bar that fits to a base that is affixed to the rodent cassette in accordance with some embodiments.
Figure 3:
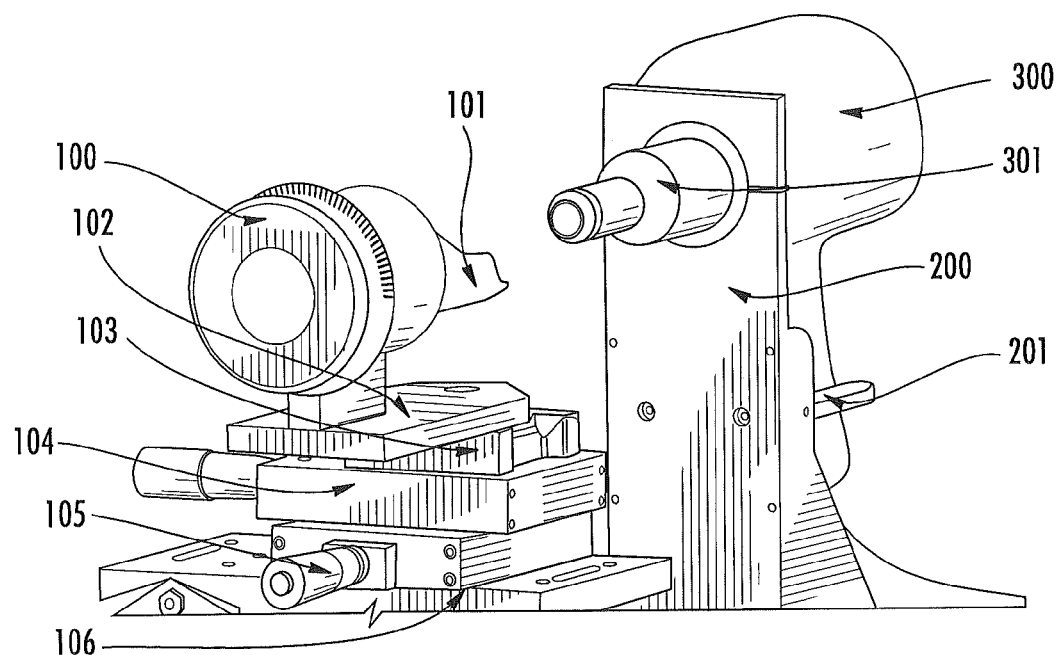
FIG. 3 is a perspective view of an imaging system, showing the location of the nodal point at the intersection of the x, y, and z axes in accordance with some embodiments.

FIG. 1 is a perspective view of the AIM-RAS stage, containing the Animal Imaging Mount (AIM) holder for the imaging probe (showing a probe in place), and the Rodent Alignment Stage (RAS) for manipulating the animal in accordance with some embodiments. FIG. 2 is a diagram illustrating an AIM-RAS system modified to include a bite bar that fits to a base that is affixed to the rodent cassette in accordance with some embodiments. FIG. 3 is a perspective view of an imaging system, showing the location of the nodal point at the intersection of the x, y, and z axes in accordance with some embodiments. The rodent eye is placed precisely so that any rotations in the system pivot about this point.

Some embodiments of the present invention will now be discussed with respect to FIGS. 1 through 3. As referred to herein, elements 100-199 refer to the RAS, elements 200-299 refer to the AIM, elements 300-399 refer to the imaging probe, and elements 400-499 refer to the bite bar. As illustrated, element 100 illustrates the housing 'gantry' for the mouse cassette 101. The mouse cassette 101 is a rotatable mount configured to receive the animal subject, and may be sized for different classes of subject, such as mouse, rat, and the like. Rotation of this cassette 101 provides the equivalent motion of changing the elevation angle of the eye with respect to lens 301 of the optical delivery system. Angular elevation degrees marked off on the back of the housing gantry 100 enable precise angular positioning. The housing gantry 100 is connected to a support structure 102 anchored by a pin to a rotary stage 103, with angular degrees marked to indicate the azimuthal angle adjustments with reference to the nodal point in the subject eye. In some embodiments of the present invention, systems are designed such that the nodal point of the subject eye is placed at the center of rotation of the rotary stage 103.

Figure 4:
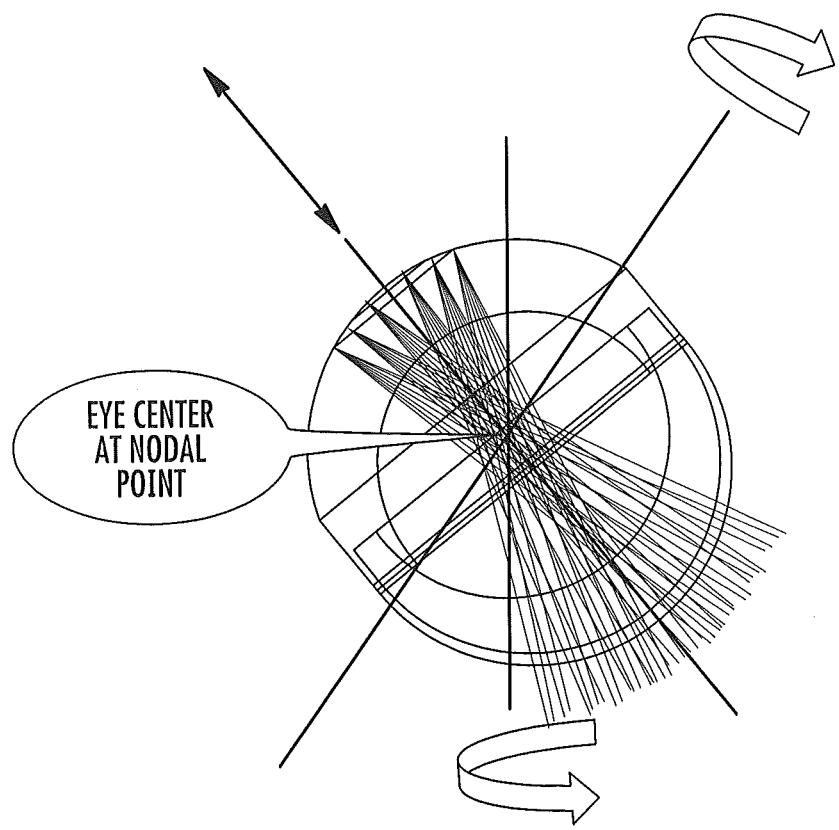
FIG. 4 is a diagram illustrating placement of the nodal point in the eye, where the ocular pivot point coincides with the nodal point in accordance with some embodiments.
Figure 5B:
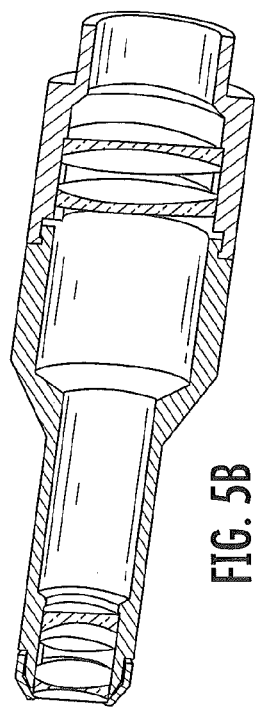
FIGS. 5A through 5D are diagrams illustrating optics for mouse and rat retinal imaging, and include the anterior segment bore in accordance with some embodiments.
Figure 5D:
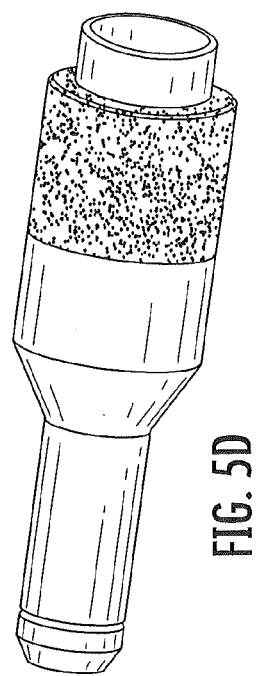
Figure 5A:
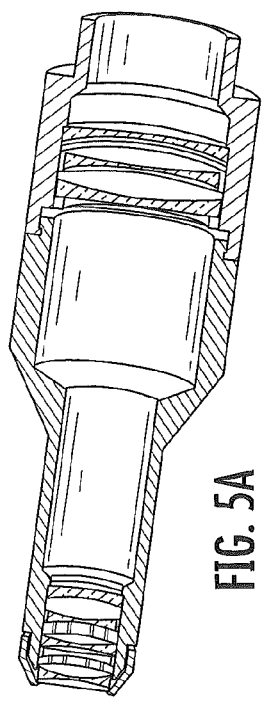
Figure 5C:
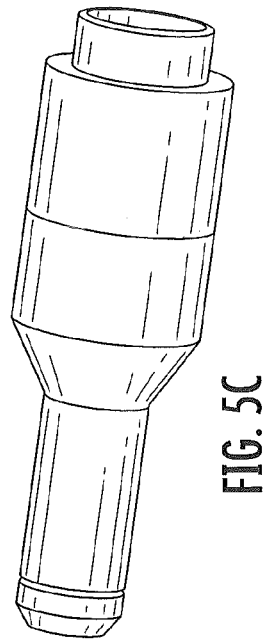

FIG. 4 illustrates placement of the nodal point in the eye, where the nodal point is approximated by the pupil, and where rotational degrees of freedom intersect at this point, allowing the system to pivot around this nodal point in accordance with some embodiments. When the nodal point and the pivot points coincide, the subject eye anatomy can be explored with either of the angular adjustments indicated by the circular arrows, i.e. the azimuthal and elevation angles.

Referring again to FIGS. 1 through 3, the combination of the cassette 101 within the housing 100 affixed to the rotation stage 103 provides two orthogonal angular degrees of freedom to facilitate alignment of the imaging optic 301 to the optical axis of the subject. The rotational system is affixed to a pair of micrometer translation stages 104 and 105 that provides Cartesian motion in a plane (x,z) parallel to the optical axis of the beam. Vertical translation is facilitated by a stage 106. The three Cartesian axes of adjustment 104, 105 and 106 supplement the rotational degrees of freedom, and are redundant by design to degrees of freedom accessible with the AIM unit 200. The RAS alignment structure is mounted to a base 107, which is in turn mounted on pillars 108 to provide a table and workspace around which other parts of the system may be placed or fed.

The AIM system 200 is a mounting apparatus for the imaging probe 300. The imaging system may, in some embodiments, be an OCT imaging probe, a video, digital or film fundus camera, a scanning laser ophthalmoscope or any similar system without departing from the scope of the present invention. The imaging system may, in some embodiments, be non-optical, and may include an ultrasound probe. For an OCT imaging system, a probe 300 is mounted to a structure defined by 200 and 201. The imaging probe 300 includes a lens 301 that may be any suitable optic for the subject. In some embodiments, the lens 301 is optimized for the subject. The lens 301 could be one of a few specially designed optics for imaging mice or rat retina, or cornea in anterior segment OCT.

Figure 6A:
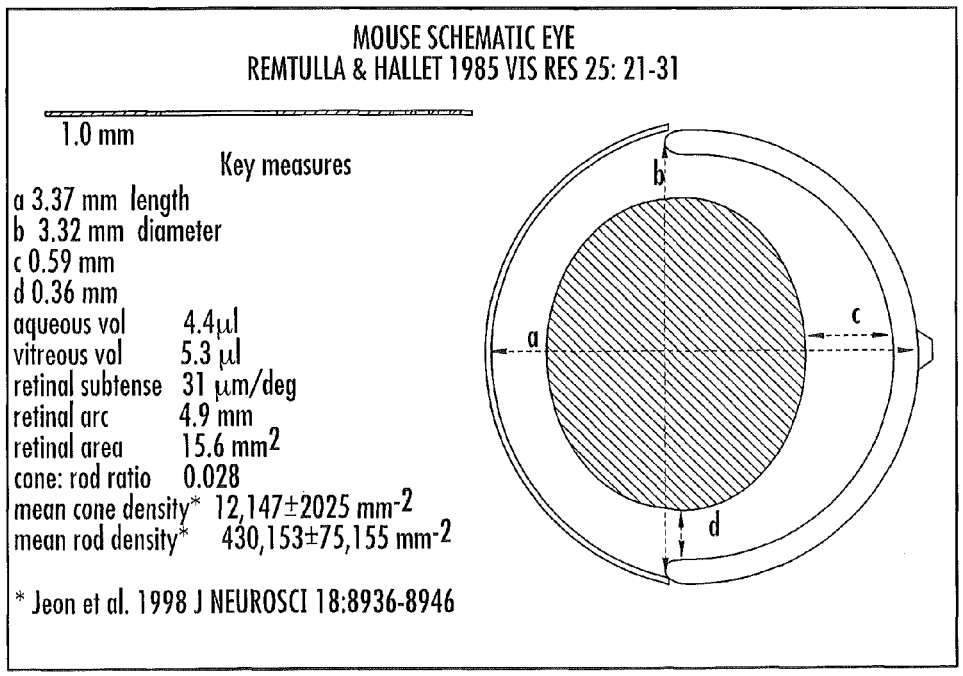
FIGS. 6A and 6B are schematics of the mouse and rat eyes, which illustrate the need for the specialized optics in accordance with some embodiments.
Figure 6B:
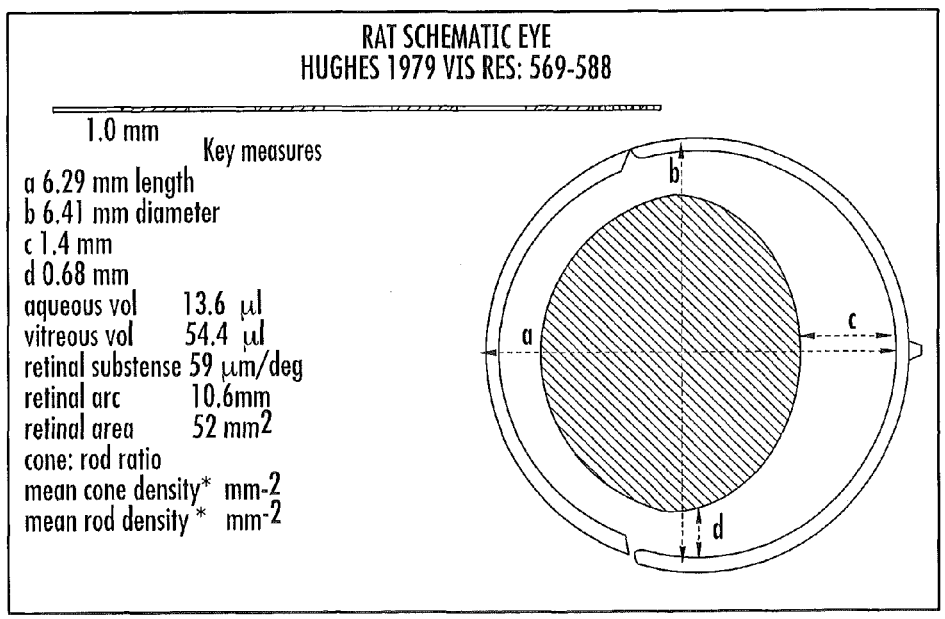

FIGS. 5A through 5D are diagrams illustrating optics for mouse and rat retinal imaging, and include the anterior segment bore in accordance with some embodiments of the present invention. The optical design addresses a problem of imaging through the ball lens of the rodent eye which is highly spherical, and lacking the power that would be found in a human eye. The optics are designed such that the field curvature of the imaging optics approximately matches the retinal curvature, with the pivot point placed at the center of the retinal curvature. FIGS. 6A and 6B are schematics of the mouse and rat eyes, which illustrate the need for the specialized optics in accordance with some embodiments.

Referring again to FIGS. 1 through 3, the alignment degrees of freedom for the AIM may include three Cartesian degrees of freedom plus one or two rotational degrees of freedom. Motion in the plane defined by stages 104 and 105 of the RAS is mediated through structure 206 of the AIM. Vertical motion is facilitated by a drive mechanism 205. The mount structure rotates around a forward rotation point 207. When properly aligned, a pivot point of the optics 301, the nodal point of the subject eye, the rotation point 102 and the rotation point 207 are aligned along a single vertical, allowing controlled rotations of subject relative to the system about the nodal point of the subject.

The nodal point (FIG. 4) of the subject is an optical construct with a specific definition as a point through which a ray appears to be undeviated. Experimentally, one does not precisely identify the nodal point in an imaged subject, but the performance of the system is constructed such that there is a center of rotation within the subject eye about which rays pivot, and from which rays focus onto the retina. Practically speaking, the nodal point as used herein is within or somewhat posterior to the iris, and the iris forms an optical stop within the system. The optical system defined by lens 301 and the optical imaging constructs of the subject eye may be visualized to bring a bundle of rays from the imaging source, whether a scanning system as in OCT or a video camera, to a pivot point in the vicinity of the iris, and a focal point coincident with the retina. More specifically, the focus is surface, and in a well defined optical system the surface is conformally similar to the surface of the retina, providing maximum brightness and resolution across the broadest field of view. This conformal similarity typically only occurs when the system is well aligned, and achieving this alignment consistently is an objective of some embodiments of the present invention. The specific optics of lens 301 are discussed in commonly assigned United States Patent Publication No. 2009/0268161, published on Oct. 29, 2009, entitled OPTICAL COHERENCE TOMOGRAPHY (OCT) IMAGING SYSTEMS HAVING ADAPTABLE LENS SYSTEMS AND RELATED METHODS AND COMPUTER PROGRAM PRODUCTS, the content of which is hereby incorporated herein by reference as if set forth in its entirety.

An additional fine control for propelling the lens 301 in a direction parallel to its optical axis is provided by way of a screw-drive 202. In some embodiments, the screw has a pitch of ½' per 20 turns (0.8 mm per turn). The screw may have an associated reference scale, and may include a quick release mechanism for returning the attached image capture device to a pre-selected position. A rodent eye can be from about 3.0 mm to about 10.0 mm in diameter, and a retina is approximately 1.0 mm thick, with individual layers being from about 50 µm to about 100 µm. A screw pitch of 800 µm per turn, or 100 µm per ⅛ turn, is well matched to the level of precision desired in driving an optical imaging system forward along the optical axis. More importantly, this screw pitch may be matched to the pitch of the reference arm in an OCT system, which will be discussed further below.

An OCT imaging system is an interferometric device for recording a back-scattered signal intensity from a sample through an interference of the signal with a reference signal. OCT systems are well known in the art. OCT systems may be constructed in time domain (TD-OCT) or Fourier Domain (FD-OCT) implementations. TD-OCT records a direct signature proportional to the level of backscattering at a location in the sample that is path-matched to the reference path. Obtaining a full depth image involves scanning a reference arm across a distance that corresponds to the range of interest within the sample. The interference is referred to as "coherence-gated," because a signature above noise is only recorded when the sample and reference path lengths are equivalent to within an optical path length equivalent to the coherence length of the source. The "coherence-gate" is made short, and the resolution fine, buy using a broadband source with a correspondingly short coherence length. Typical source bandwidths for retinal imaging are about 40 nm or greater, with resolutions (in air) of about 6 µm or less at a central wavelength of about 840 nm.

Fourier domain techniques rely on a Fourier transform relationship between time and frequency domains. By sampling an interferometric signal as a function of wavelength (frequency) instead of position (time), a spectral interferogram is collected that may be Fourier transformed into a depth resolved spatial scattering signature. The subject of Fourier Domain OCT is well known in the art. FD-OCT and differs fundamentally from TD-OCT in that a reference arm is not scanned through the subject to collect the scattering signature, rather the reference arm is static, and the wavelengths are collected from the relevant depth either in parallel in a spectrometer based system (referred to as Spectral Domain OCT, SD-OCT), or serially using a rapidly frequency-tuned source (Swept Source OCT, SS-OCT). The latter two implementations are functionally equivalent once the spectrum is acquired.

Though the reference arm is static during image acquisition, there is an optimum position of the reference path length for a given path of the sample arm and a given subject. Proper adjustment of the reference arm is critical for quality imaging.

In some embodiments of the present invention, a method and apparatus for optimizing the reference position in conjunction with the optics has been developed. In particular, as mentioned, the focal field of the optics is conformally similar to the shape of the retina. When the optics are aligned such that these conformal surfaces coincide, the image field appears flat (the difference between the focal field and the object plane is zero). Such a circumstance can occur at continuum of offset positions between the lens 301 and the subject when the lens presents a telecentric field to the subject. While such an optical design is plausible, and common in adult retinal imaging, the lens may not be strictly telecentric. Regardless, for any particular alignment of the optics to the subject, there is an optimum position of the reference arm such that the interferometric path length matching position is appropriately correlated to the focal conditions of the optics.

In some embodiments, a particular signature of appropriate alignment of the optics is a flattened image of the retina. However, the focal image is only apparent because of coordination with the path length matching condition. In fact, an image derived from the interferometry can be visible with improper focus, but the converse is not true. The problem then becomes one of co-optimization of focus and path length matching over a broad range of subjects and optics. Some embodiments of the present invention address this problem.

When the focal conditions are not perfectly met, but are close, it will generally be possible to find a path length matching condition through modification of the reference arm length such that a coherently derived image is visible. Some embodiments may simplify the optimization process by providing a coordinated path length adjustment process. When an OCT imaging condition is achieved, though perhaps not optimized, the path length of the sample arm that may under some optical design conditions impact the focal plane, may be adjusted in a manner coordinated with the reference arm to optimize the focal conditions while maintaining the appropriate path matching condition. Telecentric scanning optics for an emmotropic subject will image correctly independently of the distance between the imaging lens and the cornea. This condition is not met in general, in some specific instances the imaging lens has significant optical power, and in such a case the back focal plane is strongly influenced by the distance between the lens and the cornea. In such a general condition, the back focal plane may be deeper than, or shallower than the retina. The result will be an image that causes the retina to be curved—the center will appear deeper in the former condition, and shallower in the latter. Changing the sample distance will in such a circumstance necessitate a change in the reference arm length in order to maintain interferometric path matching. In some embodiments of the present invention, the imaging lens may be moved relative to the sample—thus changing the sample arm length—using the screw drive 202. Screw drive 202 is designed specifically to correlate to the reference arm drive—in some embodiments a 1:1 drive ratio, such that the sample arm length and the reference arm are driven in unison, or in a manner prescribed by a relationship between an optical path length to the sample position and a change in working distance. Details of this mechanism are discussed in commonly assigned United States Patent Publication No. 2009/0268161, published on Oct. 29, 2009, which has been incorporated by reference above. The imaging result as the relative sample position—and reference arm length—are adjusted is that the apparent curvature of the image is modified. The image may be driven from an upward curvature, through a flattened image, to a downward curvature, according to the optics. The correct optical condition is directly identified as that which optimizes the focal condition, and the image appears flat.

To complete the facilitation of optical alignment, some embodiments of the present invention provide for a specifically designed bite bar. Bite bars are used to steady an animal subject for imaging. The bite bar 400 (FIG. 2) in accordance with some embodiments provides additional functionality to facilitate localization of the nodal point (FIG. 4) of the subject eye with the center of rotation of the alignment system, as defined be the intersection of the center of rotation of the animal cassette 101, and the rotation of the cassette housing about the pin in the mounting plate 102, subject to the alignment conditions defined above.

Figure 8:
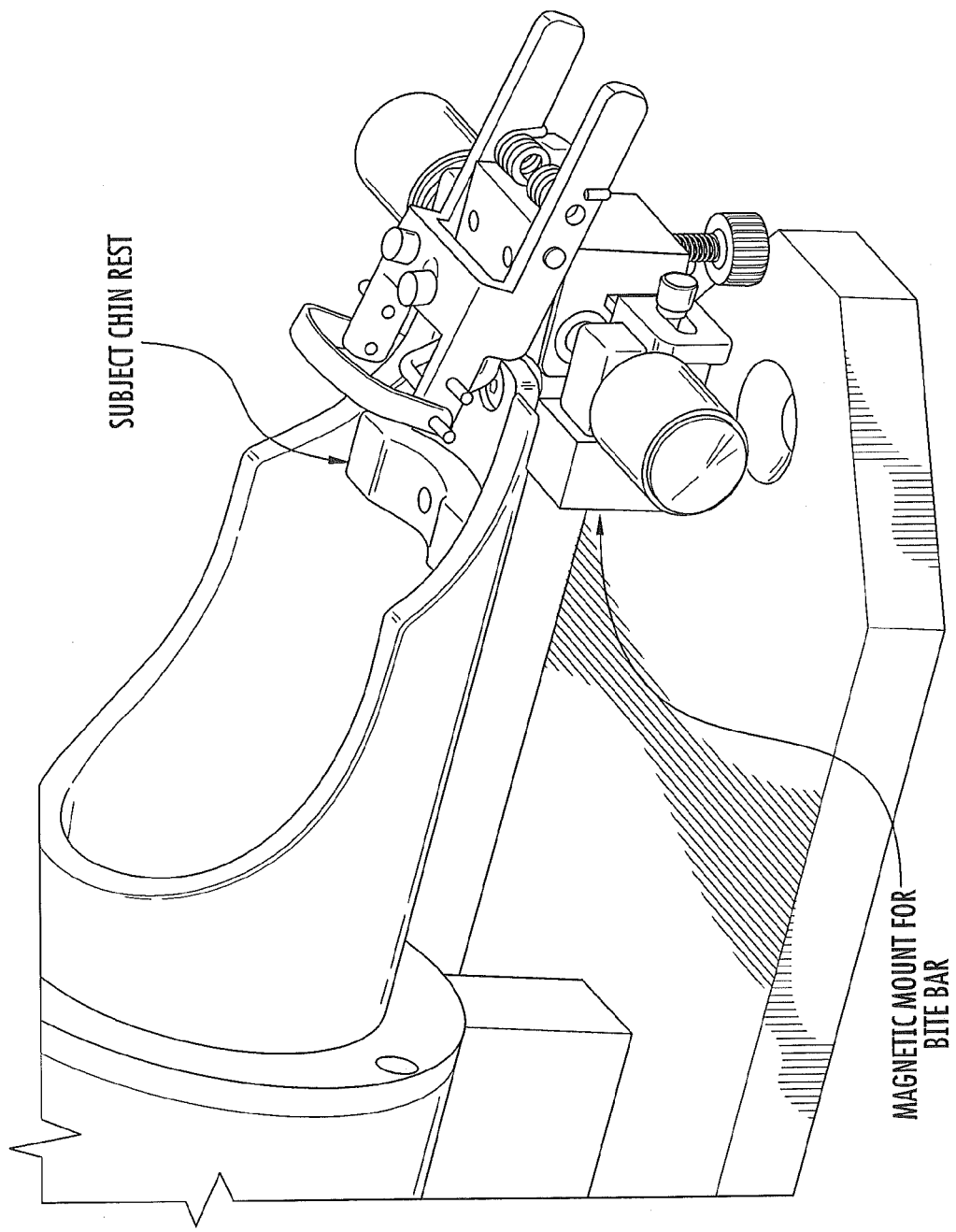
FIG. 8 is a diagram illustrating a mouse cassette with bite bar, indicating the rodent chin rest for proper elevation of head in accordance with some embodiments.
Figure 9:
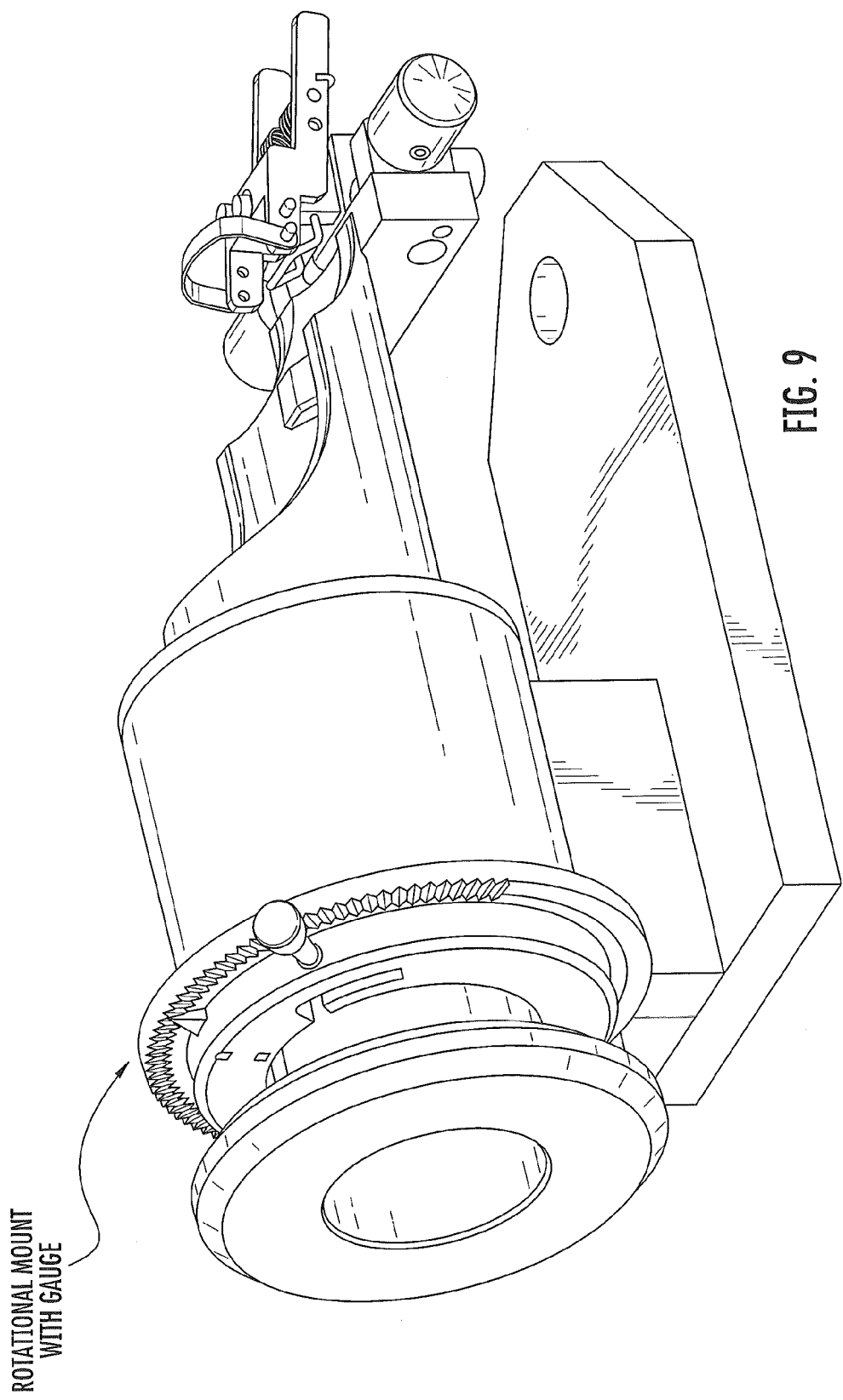
FIG. 9 is a diagram illustrating a mouse cassette with bite bar, indicating rotation compass in accordance with some embodiments.
Figure 10:
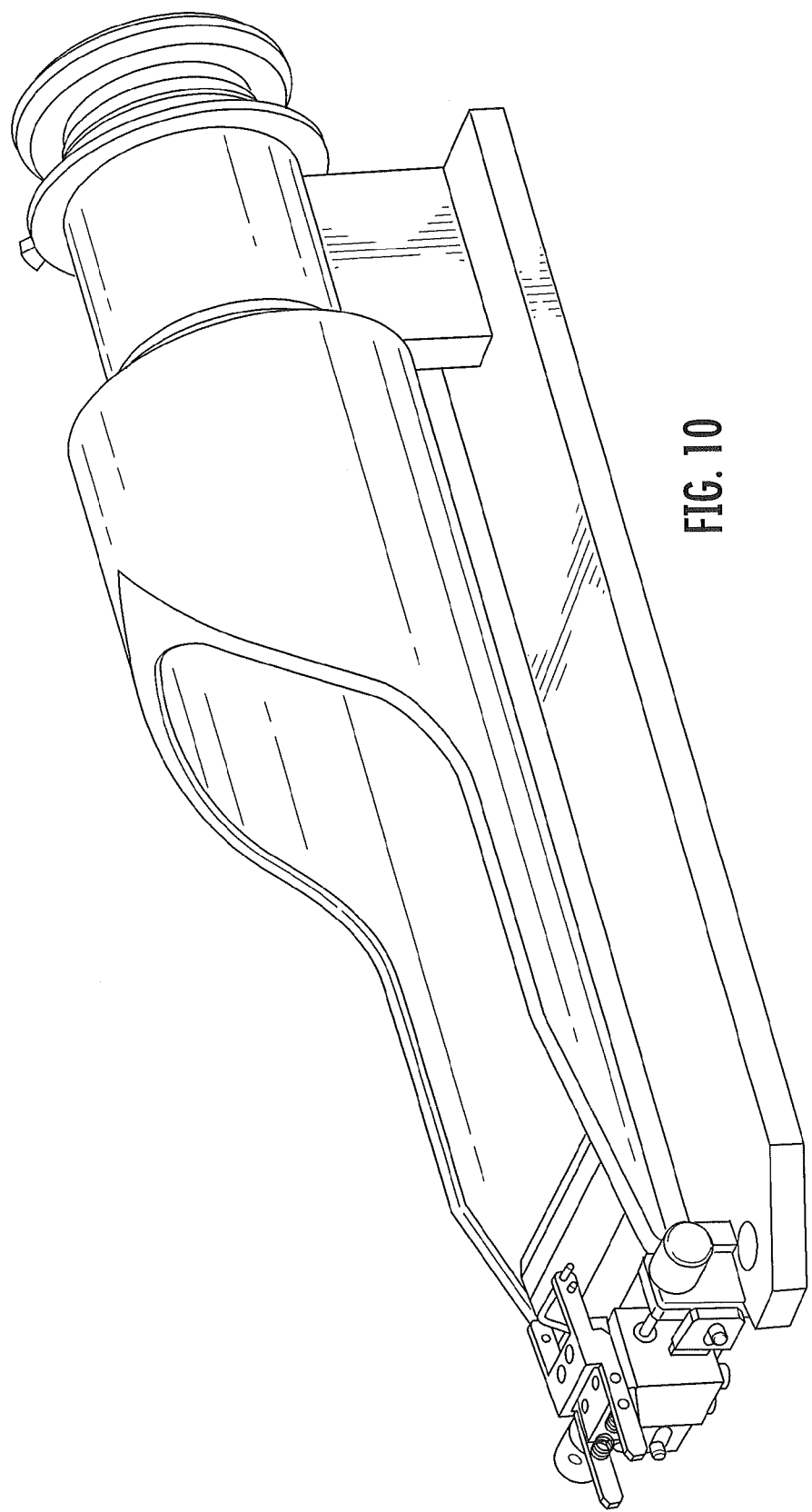
FIG. 10 is a diagram illustrating a large rodent/rat cassette with bite bar in accordance with some embodiments.
Figure 11:
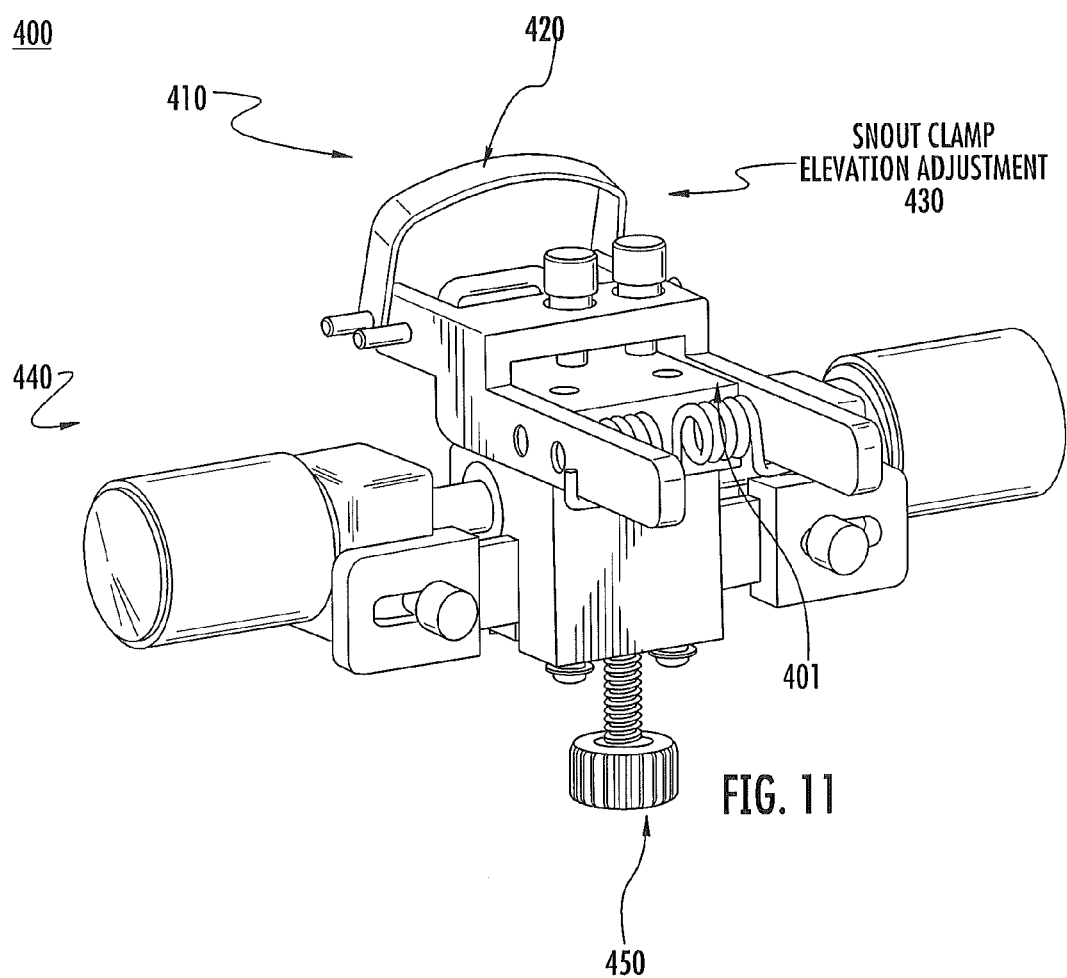
FIG. 11 is a diagram illustrating a bite bar in accordance with some embodiments.
Figure 12:
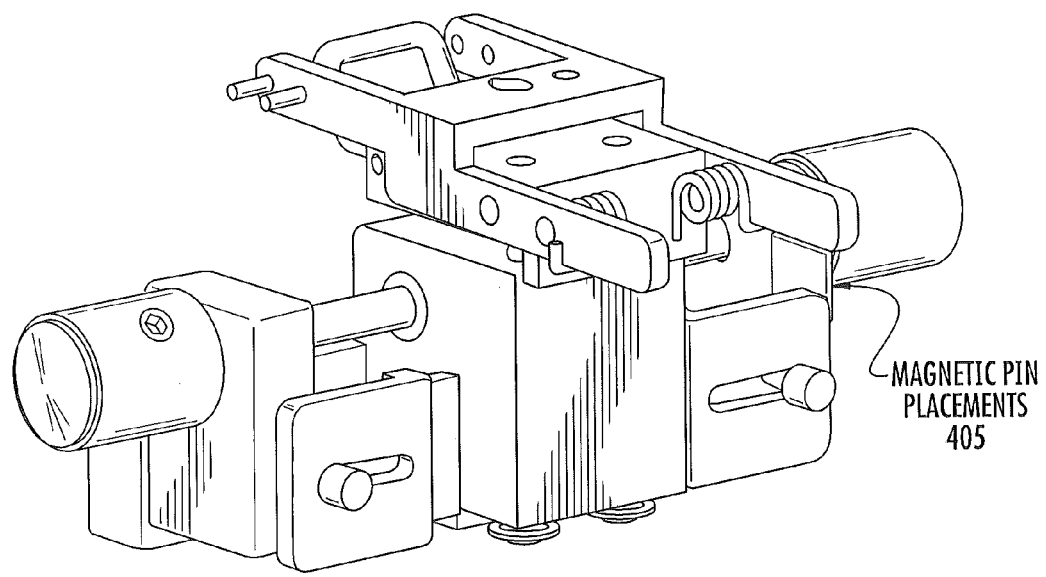
FIG. 12 is a diagram illustrating a bite bar in accordance with some embodiments.
Figure 13:
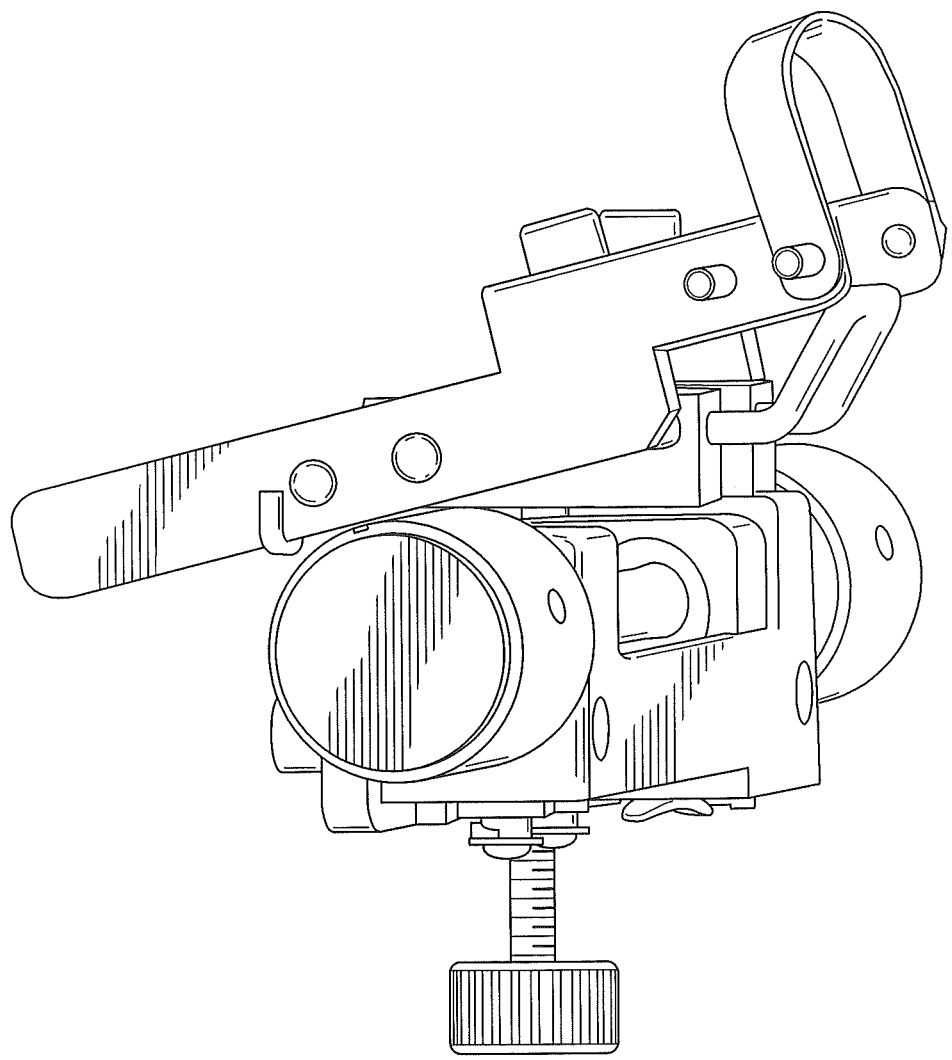
FIG. 13 is a diagram illustrating a side view of a bite bar in accordance with some embodiments.
Figure 14:
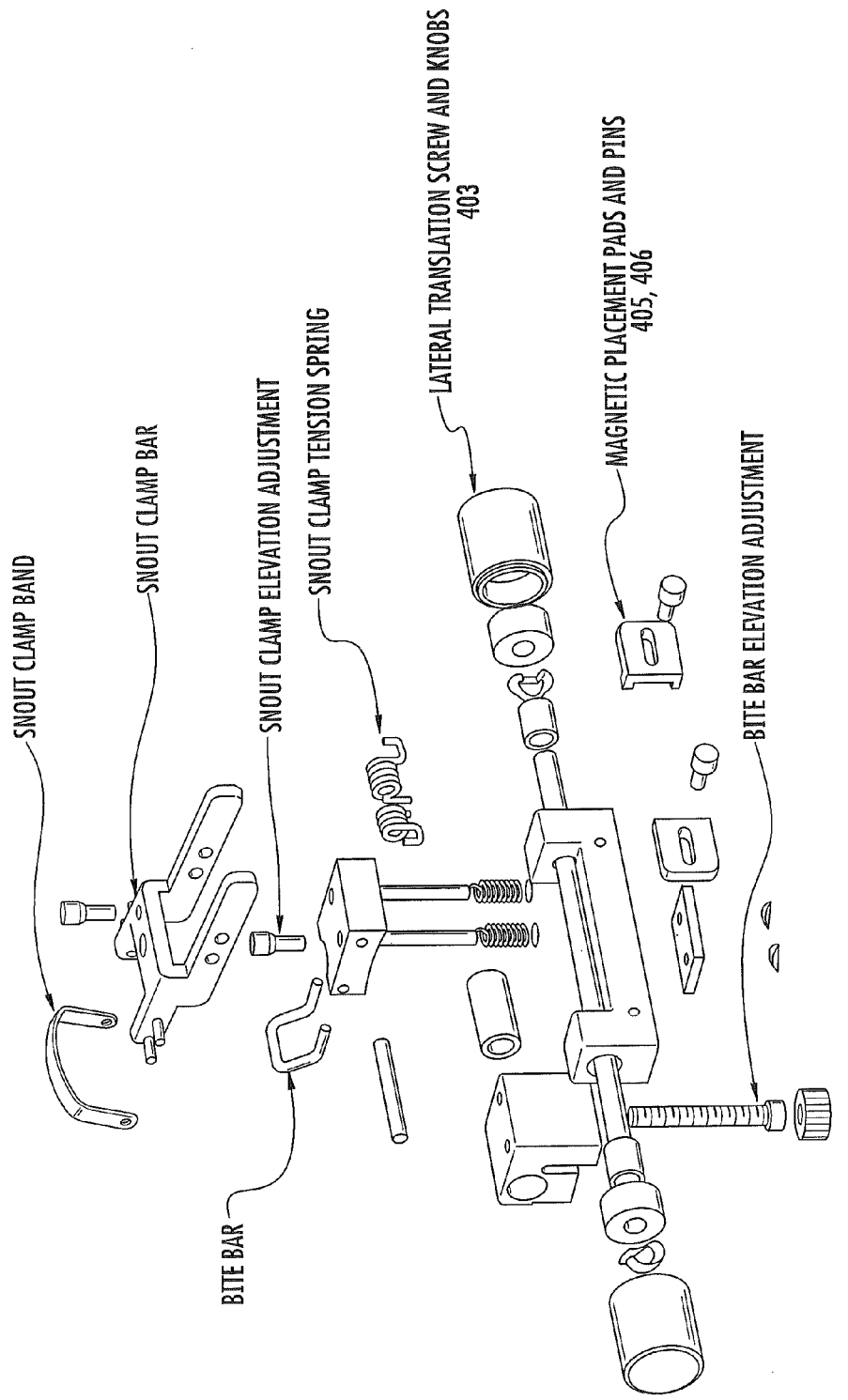
FIG. 14 illustrates an exploded view of a bite bar in accordance with some embodiments.

Various embodiments of bite bars according to embodiments of the present invention are illustrated in FIGS. 7 through 14. FIG. 7 is a diagram illustrating a mouse cassette with bite bar in accordance with some embodiments. FIG. 8 is a diagram illustrating a mouse cassette with bite bar, indicating the rodent chin rest for proper elevation of head in accordance with some embodiments of the present invention. FIG. 9 is a diagram illustrating a mouse cassette with bite bar, indicating rotation compass in accordance with some embodiments of the present invention. FIG. 10 is a diagram illustrating a larger rodent/rat cassette with bite bar in accordance with some embodiments of the present invention. FIG. 11 is a diagram illustrating an assemble view of a bite bar in accordance with some embodiments of the present invention. FIG. 12 is a diagram illustrating a bite bar having magnetic pin placements in accordance with some embodiments of the present invention. FIG. 13 is a diagram illustrating a side view of a bite bar in accordance with some embodiments of the present invention. FIG. 14 is an exploded view of a bite bar in accordance with some embodiments of the present invention.

Referring now to FIGS. 7 through 14, the bite bar 400 secures the snout of the subject animal with a bit 420, and securing strap 410. The pressure of the securing strap 410 is controlled by spring reliefs 430. The bite assembly 401 is driven laterally by lateral screw 440, and may be raised and lowered by elevator 450. The bite bar 400 further includes an ease of use feature that is attached to and removed from the cassette 101 as it is secured by pin placement 405 and held magnetically 406.

Furthermore, it is generally desirable to be able to image either the right or the left eye, and once alignment is achieved in one to be able to switch to the other with a minimum realignment. In some embodiments, flipping from one eye to the other is simplified by the symmetry of the geometry. The cassette housing may be rotated quickly from right to left, and with the bite bar the left eye moved into the final correct later position with the lateral drive screw 403, without necessitating any major adjustment in path length positions, focal positions, or heights.

Systems in accordance with some embodiments of the present invention provide an open, flexible geometry that facilitates the addition of other tools useful in alignment, imaging, therapy, or animal management. Some embodiments of the present invention an integrated heater for warming the subject in the mount/animal cassette 101. For example, in some embodiments, the animal cassette 101 (FIG. 1) may include radiator tubes aligned in the bottom of the cylindrical place where the subject may be placed. Warm water/gas may flow through the tubes to provide an insulated electrical heater. The animal cassette 101 may be designed with radiator tubes molded directly into the boy of the cassette, such that warm water/gas may be run directly to keep the cassette warm. The temperature of the subject may impact the subject physiologically. For example, if the subject, for example, a rodent, is cold, the rodent's eyes may cloud over causing the image to be distorted or the rodent to die. Providing a heated cassette 101 may not only create a more comfortable environment for the subject, but may also help to decrease or possibly avoid these physiological effects. In alternative embodiments, a heating blanket that may be a warm water blanket or an electric blanket may be used.

In some embodiments of the present invention, a fiducial indicator 510 (FIG. 15) to provide evidence of the center of rotation of the system may be provided. Referring to FIG. 15, the system may include a precision mounted mechanical fiducial assembly 500 or laser pointer, or crosshair calibrated to the center of rotation to facilitate animal placement. In some embodiments, the fiducial assembly 500 may be mounted to the rotation plate 102 such that the fiducial center is located at the center of the axis of rotation. The fiducial assembly 500 includes a centration fiducial 510. The centration fiducial 510 may, but not necessarily, be an optical phantom 800 (FIGS. 16A-16C) that has lensing attributes that are representative of the subject eye, and may be imaged by the optical system to verify the system set up and performance. Furthermore, in order to increase the likelihood of proper orientation of the scanning head 300, a lens adapter 700 may be attached to the imaging lens 301. The lens adapter 700 is designed to come into immediate contact with the fiducial 510, at which point the optical distances are optimized.

Referring now to FIG. 16, an optical phantom 800 may include a lens 810 that mimics the optical properties of the subject. For a mouse, the lens may be a ball lens with a diameter of from about 2.0 mm to about 4.0 mm. At the back of the lens, a structure 820 to mimic a retina is deployed. The structure may be a layered structure from about 250 μm to about 1500 μm thick, with layers ranging in thickness from about 20 μm to 200 μm. Such layers can be created using cast polymers, or layers of translucent tape. The layers provide a context for visualizing axial resolution and imaging depth. Lateral features 830 may be embedded between the lens and the layered structure or between one or more layers. The lateral structures may be loosely woven, with feature diameters ranging between about 5.0 μm and about 500 μm. Such structures may be created by a loose fabric of threads, or may be more precisely created through a lithographic process without departing from the scope of the present invention.

Some embodiments of the present invention may provide access to therapeutic ports or alternative diagnostics. For example, the use of a syringe to inject a chemical compound, or to guide a laser for photodynamic therapy, or a transducer for electrical or ultrasound measurements. The architecture of systems according to some embodiments of the present invention is designed to include the placement of such ancillary features that do not interfere with the optical imaging system, and in fact allow imaging during the course of therapy.

Small animal imaging systems in accordance with some embodiments of the present invention are designed to provide for optimally aligned high-quality images of a rodent eye, to provide for larger field of view (FOV) through rotations around the nodal point of the rodent eye. An alignment system has been created with the appropriate degrees of freedom to identify, align and steer around the nodal point of the subject eye. The optics appropriate for imaging the differential structure of the rodent eye, have been designed to work with a reference arm assembly in the OCT system. The mouse cassette can be modified to include a heating pad, a nose cone for gas anesthesia, and a bite bar for anchoring the rodent head in the optimal position to allow for manipulations with needles or droppers. Mouse and rat eye model phantoms have also been created to aid in system calibration and alignment.

Figure 17:
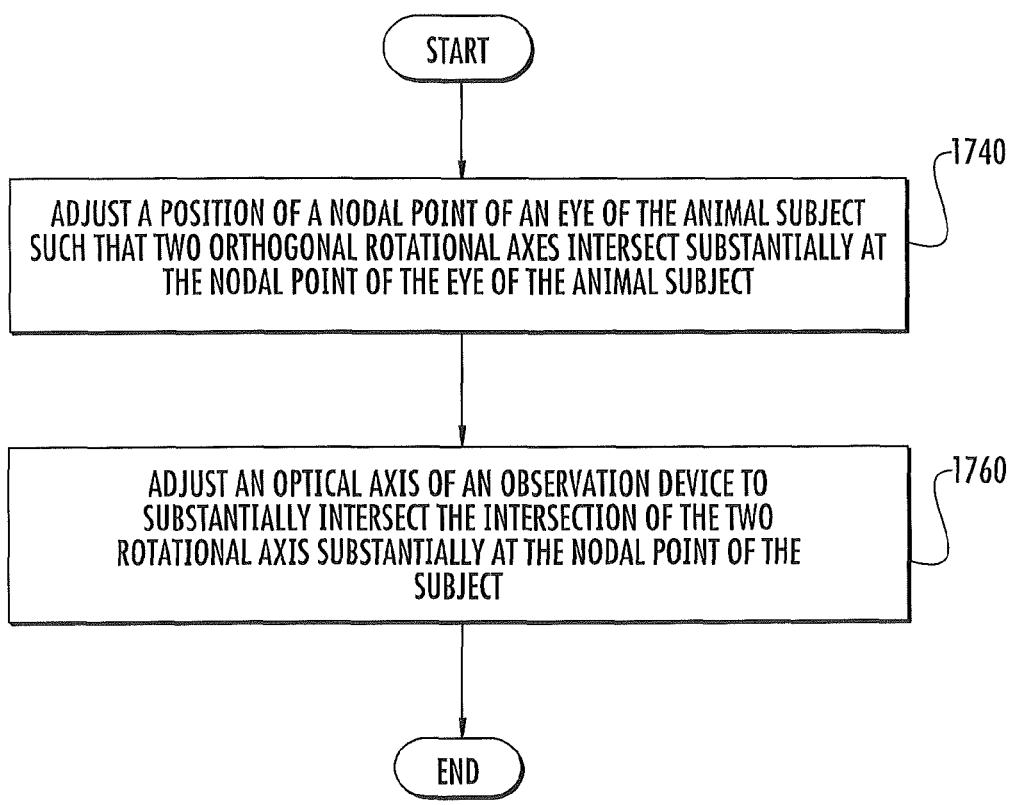
FIGS. 17-19 are flowcharts illustrating various methods in accordance with some embodiments.

Various methods for imaging an eye of an animal subject will now be discussed with respect to the flowcharts of FIGS. 17 through 18. Referring first to FIG. 17, operations begin at block 1740 by adjusting a position of a nodal point of an eye of the animal subject such that two orthogonal rotational axes intersect substantially at the nodal point of the eye of the animal subject. An optical axis of an observation device is adjusted to substantially intersect the intersection of the two rotational axis substantially at the nodal point of the subject (block 1760).

Figure 18:
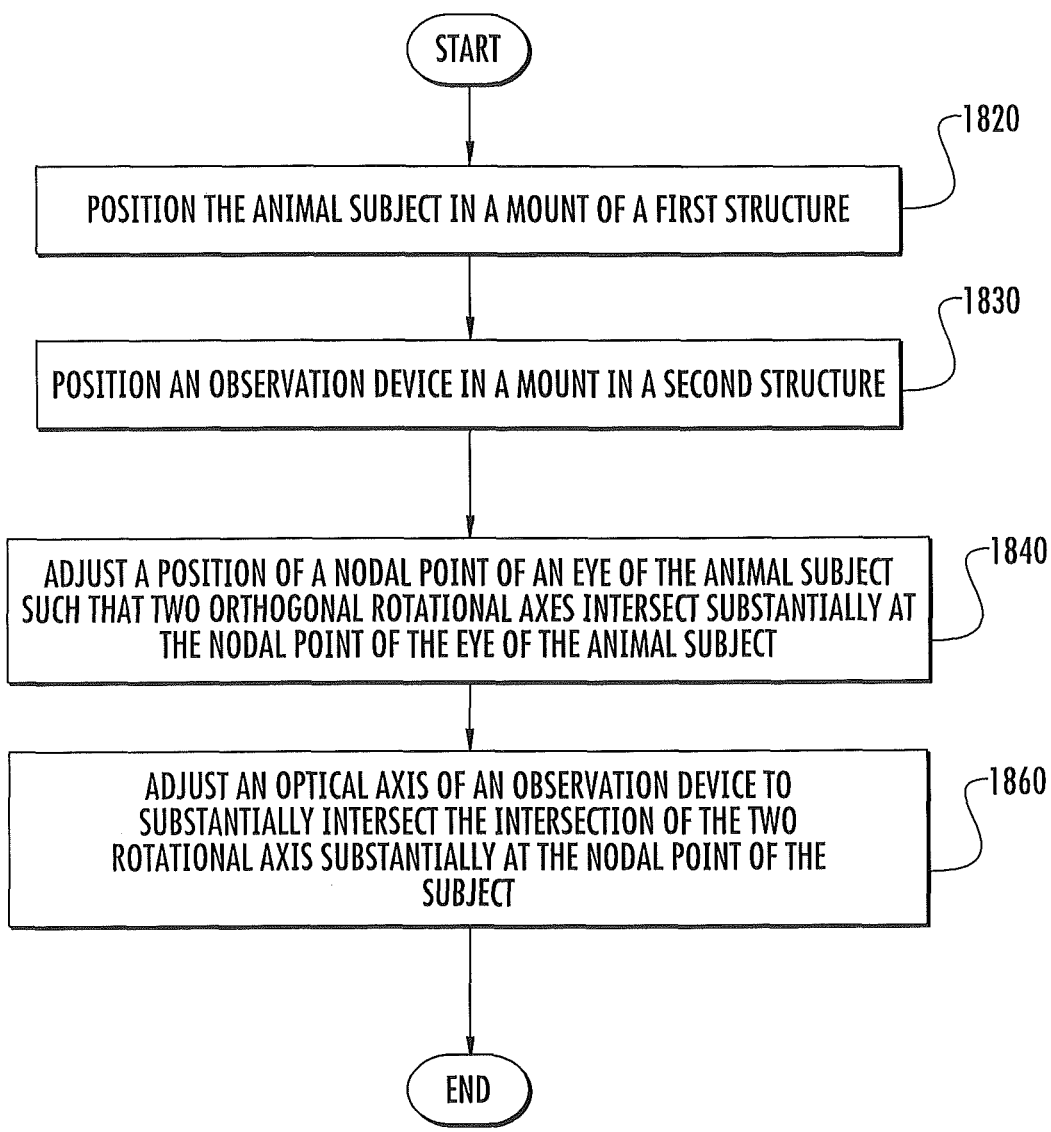

Referring now to FIG. 18, operations begin at block 1820 by positioning the animal subject in a mount of a first structure. The observation device is positioned in a mount in a second structure (block 1830). In some embodiments, positioning the animal subject includes positioning the animal subject in the mount of the first structure using a bite bar. The bite bar may have a translational axis and an elevation axis. The observation device may be an image capture device or an object configured to be peered through without departing from the scope of the present application.

A position of a nodal point of an eye of the animal subject may be adjusted such that two orthogonal rotational axes intersect substantially at the nodal point of the eye of the animal subject (block 1840). An optical axis of an observation device is adjusted to substantially intersect the intersection of the two rotational axis substantially at the nodal point of the subject (block 1860). In certain embodiments, the nodal point of the eye of the animal subject may be approximated by a pupil of the animal subject.

Figure 19:
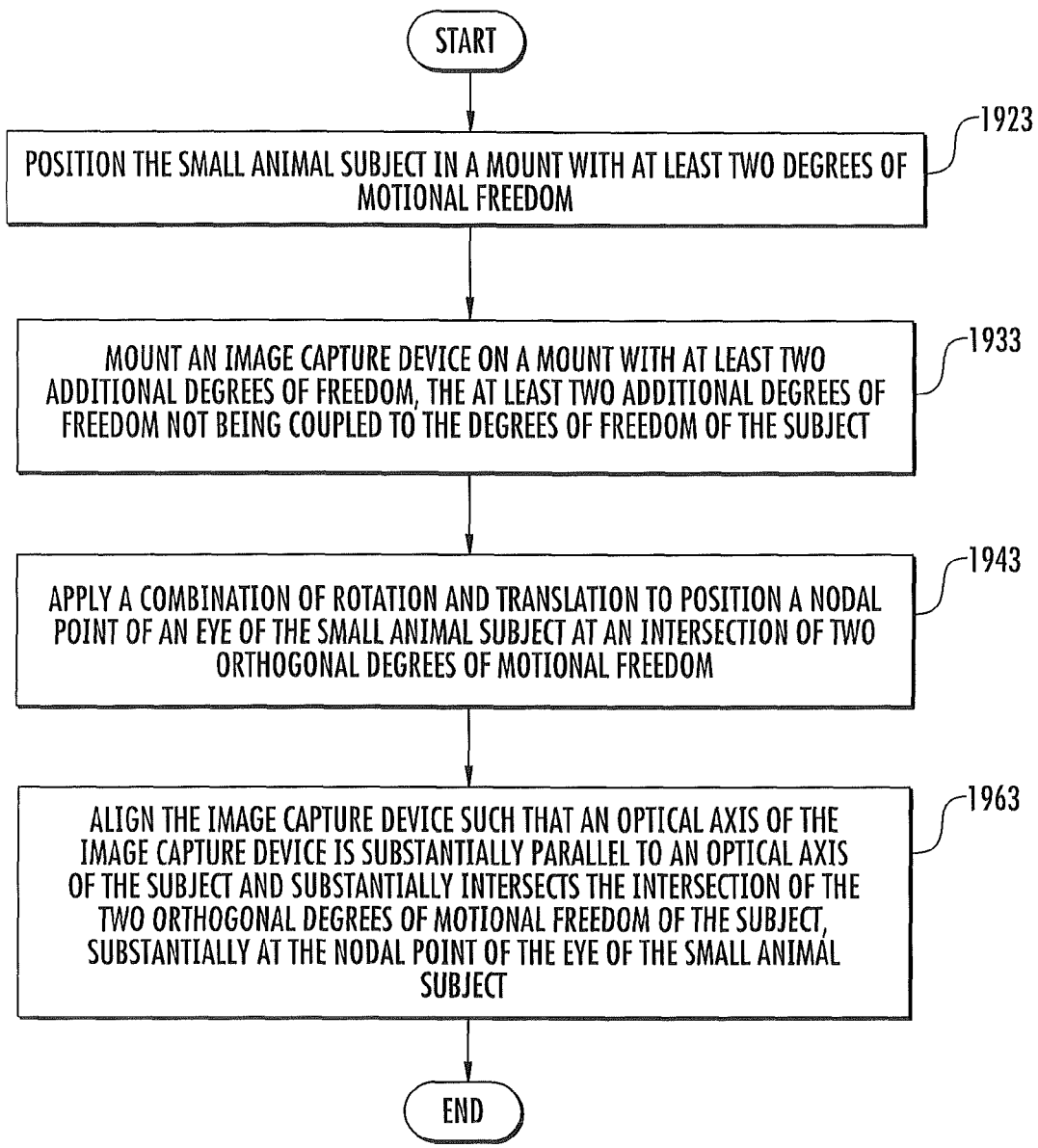

Referring now to FIG. 19, operations begin at block 1923 by positioning the small animal subject in a mount with at least two degrees of motional freedom. An image capture device may be mounted on a mount with at least two additional degrees of freedom, the at least two additional degrees of freedom not being coupled to the degrees of freedom of the subject (block 1933). A combination of rotation and translation may be applied to position a nodal point of an eye of the small animal subject at an intersection of two orthogonal degrees of motional freedom (block 1943). In some embodiments, the nodal point of the eye of the small animal subject may be approximated by a pupil of the small animal subject. The image capture device may be aligned such that an optical axis of the image capture device is substantially parallel to an optical axis of the subject and substantially intersects the intersection of the two orthogonal degrees of motional freedom of the subject, substantially at the nodal point of the eye of the small animal subject (block 1963).

As discussed briefly above with respect to FIGS. 1 through 19, high-throughput small animal imaging systems in accordance with some embodiments of the present invention include an optical alignment system that decouples lateral and rotational degrees of freedom for managing imaging of the particular ocular geometries of small animals, such as rodents and small monkeys. Systems in accordance with some embodiments of the present invention include a stage with an imaging mount capable of translating an imaging probe about multiple degrees of freedom around a small animal stage equipped with an animal-specific rotational cassette having translational and rotational degrees of freedom to manipulate the animal head. The manipulation of the animal eye is done about an optical nodal point, and allows the operator to optically explore the rodent retina with precision using systematic micro-manipulations. Systems in accordance with some embodiments of the present invention provide for rapid and precise placement of both eyes, with shifts from left and right by way of a quick lateral shift. The assembly can be modified to image both rodent posterior (retina) and anterior segment with specially-designed optical bores and coordination of reference arm optical path lengths for optical coherence tomography imaging. The system may include a heating pad to keep the animal temperature within a range. The assembly may be modified also to include needle-guided apparatus or other apparatus that needs access to the rodent eye during imaging without moving the animal from the optimal imaging position. The small animal stage may include a bite bar to reduce the likelihood animal head motion during such procedures, and a nose cone for administering gaseous anesthesia.

In the drawings and specification, there have been disclosed exemplary embodiments of the invention emphasizing the utility for imaging animal subjects. However, many other subjects may benefit from the general embodiments of this invention. Any subject that possess a nodal point, and particularly subjects for which, like the eye, it is desirable to image through an optical stop to features posterior to the stop may benefit from the application of embodiments of this invention. For example, it may be desirable to image phantom eye models with embodiments of this invention.

In the drawings and specification, there have been disclosed exemplary embodiments of the invention. However, many variations and modifications can be made to these embodiments without substantially departing from the principles of the present invention. Accordingly, although specific terms are used, they are used in a generic and descriptive sense only and not for purposes of limitation, the scope of the invention being defined by the following claims.

That which is claimed is:

1. An apparatus for positioning a small animal subject, the apparatus comprising:
   a first structure including a mount for the subject to positioned, the first structure having a cylindrical region with an inner surface and an outer surface and having an opening on at least one end;
   a second structure coupled to the first structure and including a mount for the subject to be positioned, the second structure having a cylindrical region with an inner surface and an outer surface and having an opening on at least one end, wherein an outer radius of curvature of at least a portion of the second structure is less than an inner radius of curvature of at least a portion of the first structure and wherein at least a portion of the second structure forms a platform for positioning the small animal subject; and
   a mechanism for coupling the second structure to the first structure such that the second structure is configured to rotate with respect to a first axis of rotation parallel to an axis of its cylinder region.

2. The apparatus of claim 1, wherein the small animal subject comprises one of a mammal, a fish, a bird, a reptile, an amphibian, an insect, and a mollusk.

3. The apparatus of the claim 1, further comprising a second axis of rotation orthogonal to the first axis of rotation.

4. The apparatus of the claim 3, wherein the first and second axes of rotation intersect.

5. The apparatus of claim 4, wherein the first and second axes of rotation include a rotation about a first axis substantially parallel to a first axis of symmetry of the small animal subject and a rotation about an orthogonal second axis substantially parallel to a second axis of symmetry of the small animal subject.

6. The apparatus of the claim 1, further comprising a bite bar associated with the platform of the second structure for positioning and/or restraining the subject.

7. The apparatus of the claim 1, further comprising a nose cone associated with the platform of the second structure for administering anesthesia to the subject.

8. The apparatus of the claim 1, further comprising a set of tubes embedded within at least a portion of the apparatus configured to hold and/or to flow a gas and/or a liquid.

9. The apparatus of the claim 1, further comprising an electrically isolated integrated heater for warming the subject.

10. The apparatus of the claim 1, further comprising an accessory assembly for mounting a syringe, a diagnostic device, and/or a therapeutic device.

11. An apparatus for positioning a small animal subject, the apparatus comprising:
a first structure including a mount for the subject to be positioned;
a second structure coupled to the first structure and including a mount for the subject to be positioned, wherein at least a portion of the second structure forms a platform for positioning the small animal subject; and
a means for coupling the second structure to the first structure such that the second structure is configured to rotate with respect to a first axis of rotation substantially parallel to an axis of symmetry of the small animal subject.

12. The apparatus of claim 11, wherein the small animal comprises one of a mammal, a fish, a bird, a reptile, an amphibian, an insect, and a mollusk.

13. The apparatus of the claim 11, further comprising a second axis of rotation orthogonal to the first axis of rotation.

14. The apparatus of the claim 13, wherein the first and second axes of rotation intersect.

15. The apparatus of claim 14, wherein the axis of symmetry of the small animal subject is an axis of a body that separates a right side of the small animal subject from a left side of the small animal subject and a right eye of the small animal subject from a left eye of the small animal subject.

16. The apparatus of the claim 11, further comprising a bite bar associated with the platform of the second structure for positioning and/or restraining the subject.

17. The apparatus of the claim 11, further comprising a nose cone associated with the platform of the second structure for administering anesthesia to the subject.

18. The apparatus of the claim 11, further comprising a set of tubes embedded within at least a portion of the apparatus configured to hold and/or to flow a gas and/or a liquid.

19. The apparatus of the claim 11, further comprising an electrically isolated integrated heater for warming the subject.

20. The apparatus of the claim 11, further comprising an accessory assembly for mounting a syringe, a diagnostic device, and/or a therapeutic device.

* * * * *

UNITED STATES PATENT AND TRADEMARK OFFICE
CERTIFICATE OF CORRECTION

PATENT NO.         : 8,721,080 B2                                          Page 1 of 1
APPLICATION NO.    : 14/020945
DATED              : May 13, 2014
INVENTOR(S)        : Sayeram et al.

It is certified that error appears in the above-identified patent and that said Letters Patent is hereby corrected as shown below:

On Title Page:
Item (73), Assignee: correct "Biopgtigen, Inc., Morrisville, NC (US)"
to read -- Bioptigen, Inc., Morrisville, NC (US) --

Signed and Sealed this
Twenty-fifth Day of November, 2014

Michelle K. Lee
*Deputy Director of the United States Patent and Trademark Office*